(12) United States Patent
Sadakane et al.

(10) Patent No.: US 9,036,776 B2
(45) Date of Patent: May 19, 2015

(54) X-RAY PHOTOGRAPHY APPARATUS

(71) Applicant: J. Morita Manufacturing Corporation, Kyoto-shi, Kyoto (JP)

(72) Inventors: Tomoyuki Sadakane, Kyoto (JP); Hideki Yoshikawa, Kyoto (JP)

(73) Assignee: J. MORITA MANUFACTURING CORPORATION, Kyoto (JP)

( * ) Notice: Subject to any disclaimer, the term of this patent is extended or adjusted under 35 U.S.C. 154(b) by 42 days.

(21) Appl. No.: 14/074,513

(22) Filed: Nov. 7, 2013

(65) Prior Publication Data
US 2014/0126686 A1 May 8, 2014

(30) Foreign Application Priority Data
Nov. 8, 2012 (JP) ................. 2012-246534

(51) Int. Cl.
| A61B 6/14 | (2006.01) |
| A61B 6/03 | (2006.01) |
| A61B 6/02 | (2006.01) |
| A61B 6/06 | (2006.01) |
| A61B 6/00 | (2006.01) |
| A61B 6/04 | (2006.01) |

(52) U.S. Cl.
CPC ............ A61B 6/145 (2013.01); A61B 6/032 (2013.01); A61B 6/025 (2013.01); A61B 6/035 (2013.01); A61B 6/0457 (2013.01); A61B 6/0478 (2013.01); A61B 6/06 (2013.01); A61B 6/14 (2013.01); A61B 6/4476 (2013.01); A61B 6/469 (2013.01); A61B 6/5223 (2013.01); A61B 6/545 (2013.01)

(58) Field of Classification Search
USPC ........................................ 378/38, 39, 40, 13
See application file for complete search history.

(56) References Cited

U.S. PATENT DOCUMENTS

| 6,493,415 B1 * | 12/2002 | Arai et al. ........................ 378/4 |
| 2008/0232540 A1 * | 9/2008 | Yoshimura et al. ............... 378/4 |
| 2009/0041191 A1 * | 2/2009 | Suzuki et al. ................ 378/98.5 |
| 2014/0126687 A1 * | 5/2014 | Yoshikawa et al. ............. 378/16 |

FOREIGN PATENT DOCUMENTS

| DE | 10 2010 040096 A | 3/2012 |
| JP | H4-144548 A | 5/1992 |
| JP | 2003-245277 A | 9/2003 |
| JP | P2006-34785 A | 2/2006 |
| JP | P2006-314774 A | 11/2006 |
| JP | 2007-29168 A | 2/2007 |
| JP | 2007-136163 A | 6/2007 |
| WO | WO 2009/063974 A | 5/2009 |

* cited by examiner

Primary Examiner — Kiet T Nguyen
(74) Attorney, Agent, or Firm — DLA Piper LLP (US)

(57) ABSTRACT

An X-ray photography apparatus including: a turning arm that supports an X-ray generator and an X-ray detector while the X-ray generator and the X-ray detector are opposed to each other so that a head of a patient can be interposed therebetween; and a moving mechanism that turns the turning arm about a turning axis with respect to the head and moves the turning arm in a direction perpendicular to the turning axis with respect to the head. The X-ray photography apparatus further includes: an image processor that generates an X-ray image based on an electric signal output from the X-ray detector; and a photographic region designation receiving part that designates part of a row of teeth along a dental arch as a pseudo intraoral radiography region. The image processor generates plural tomographic images by applying convolution and filtered back projection to X-ray image data obtained by pseudo intraoral radiography.

19 Claims, 27 Drawing Sheets

F I G . 1
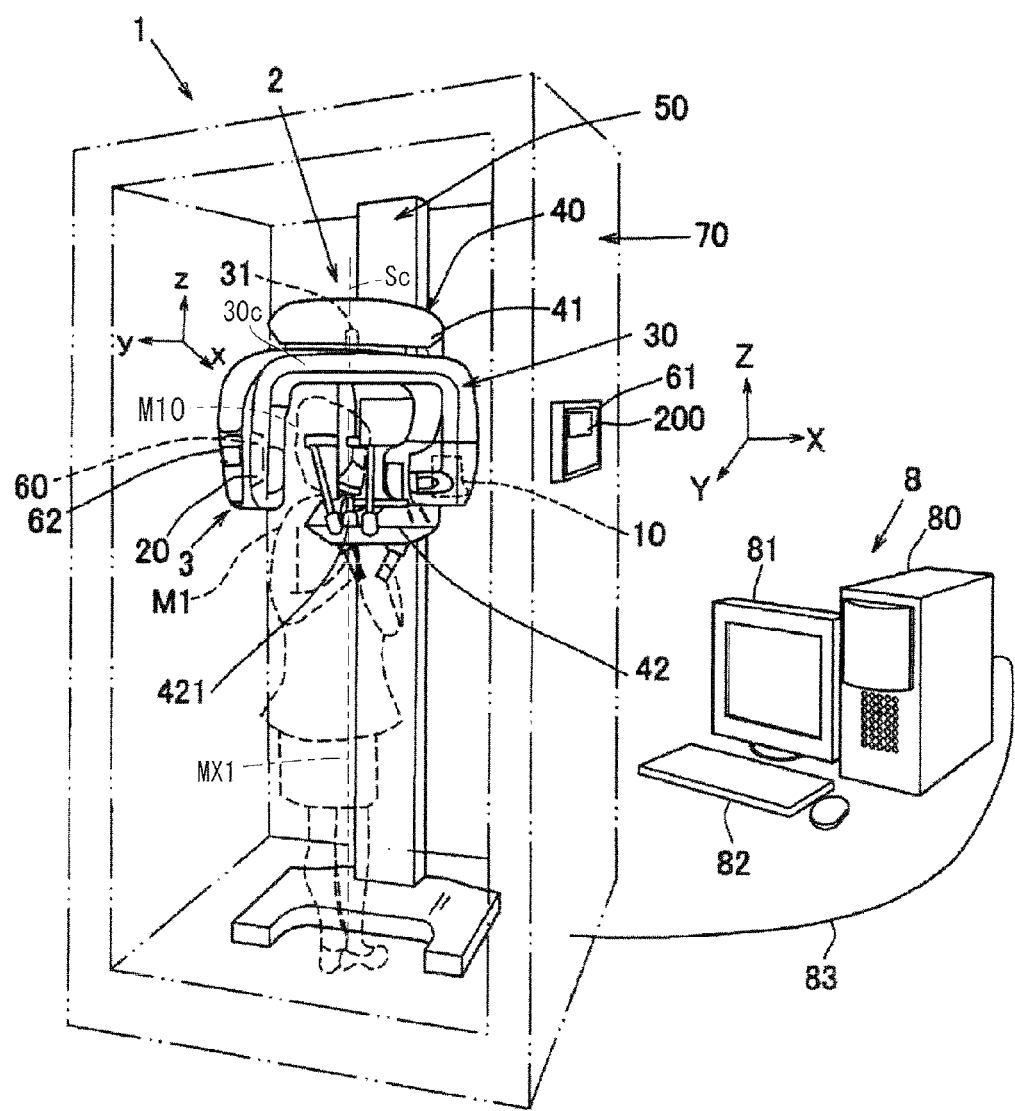

F I G. 3
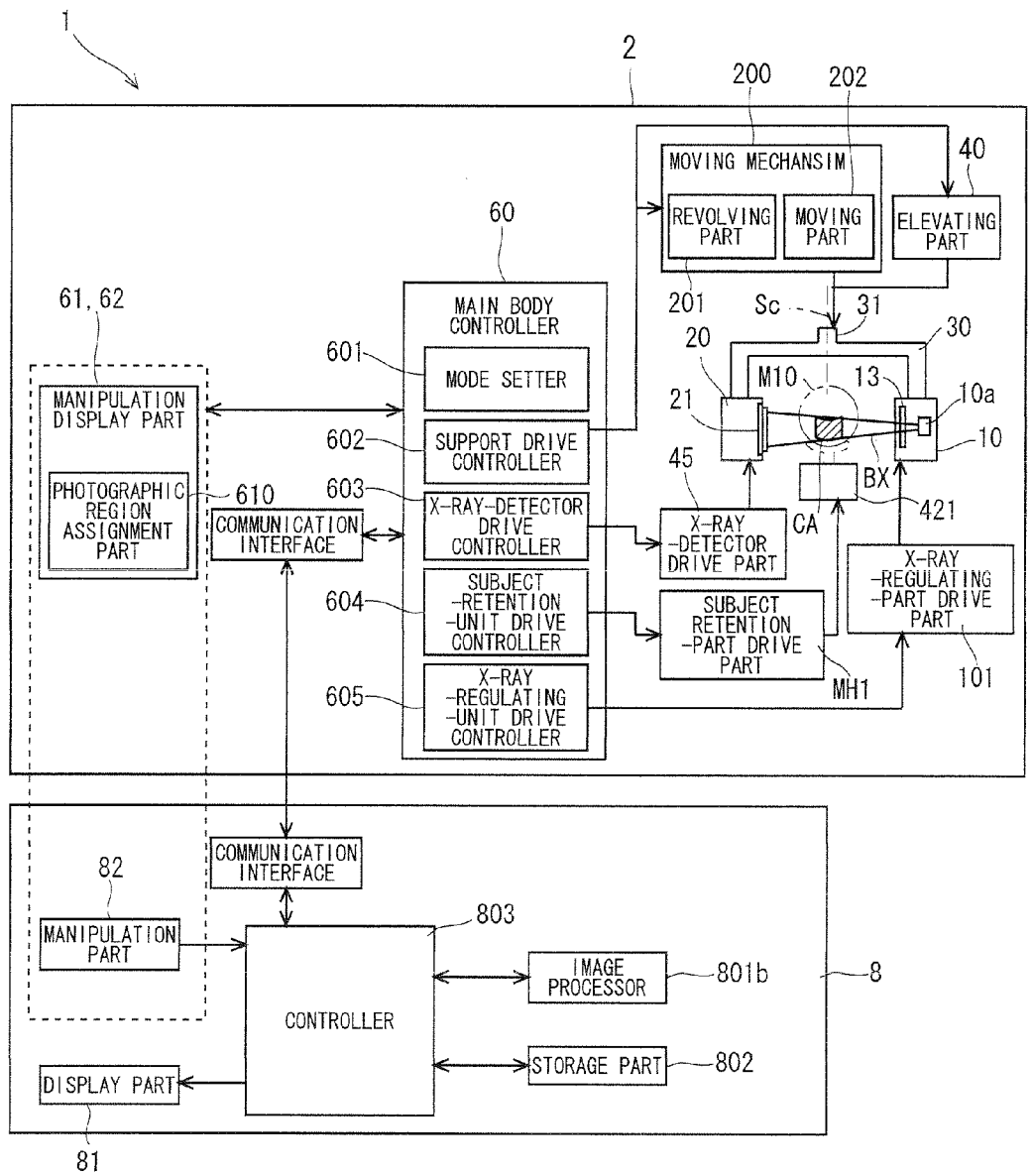

F I G . 6
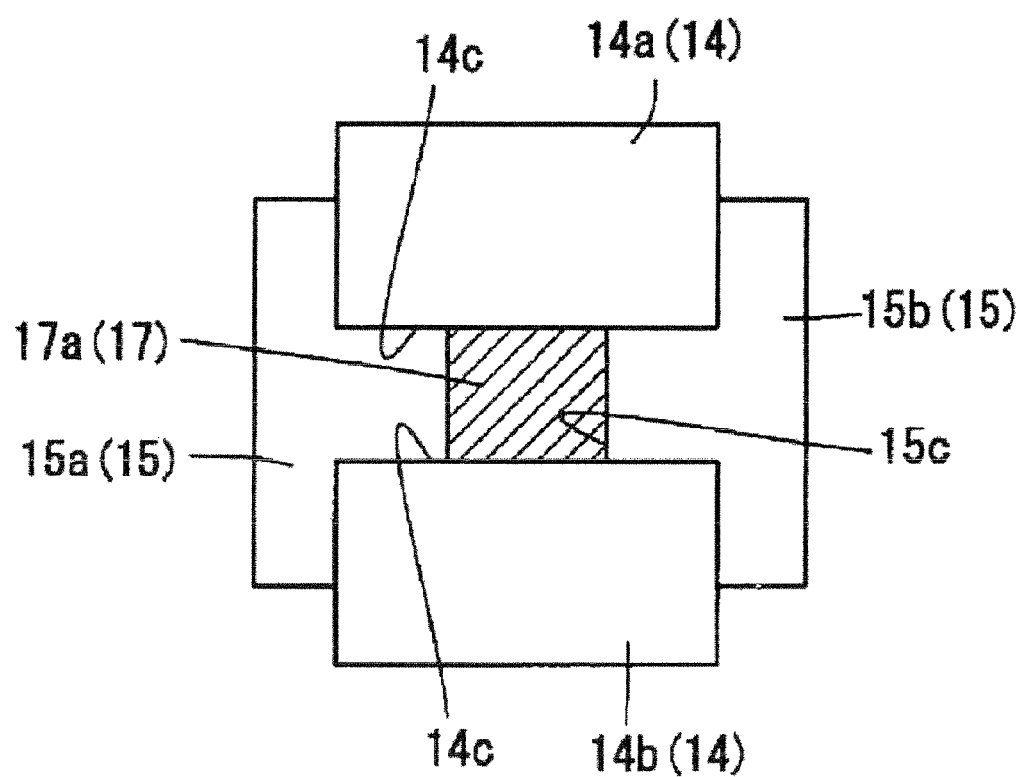

F I G . 1 0
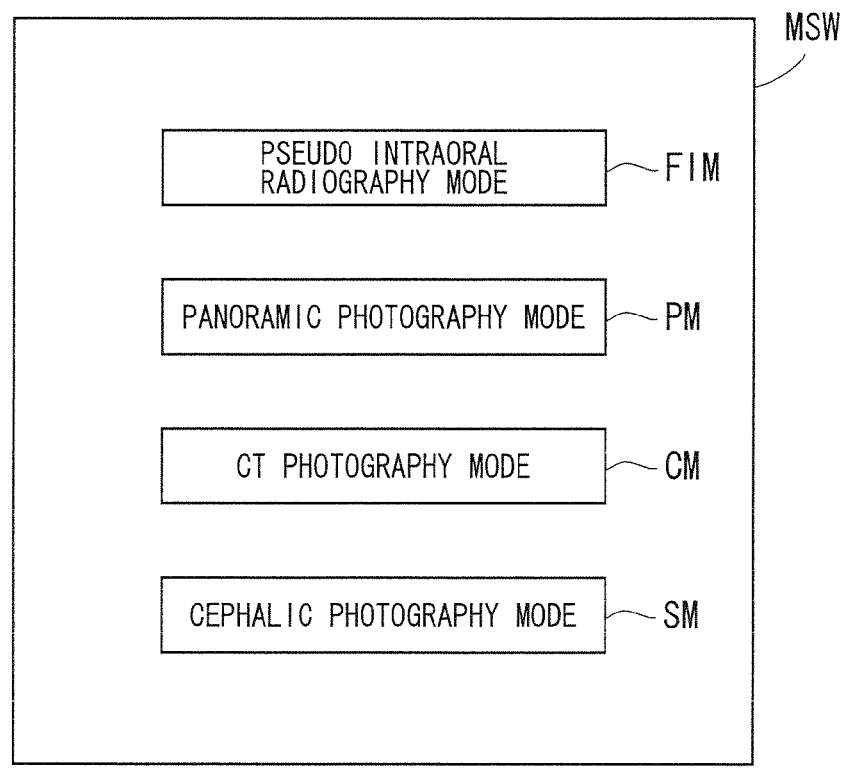

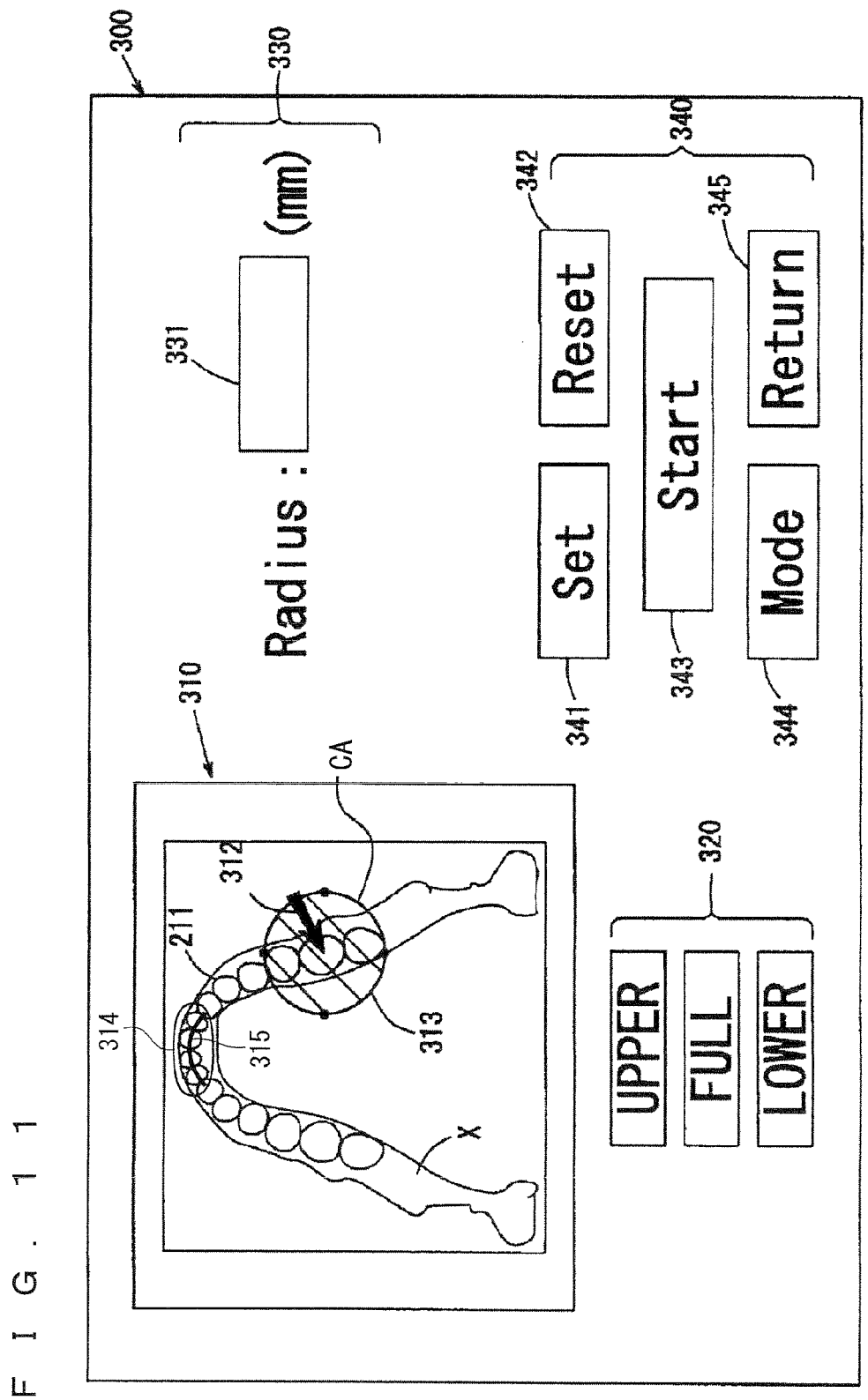

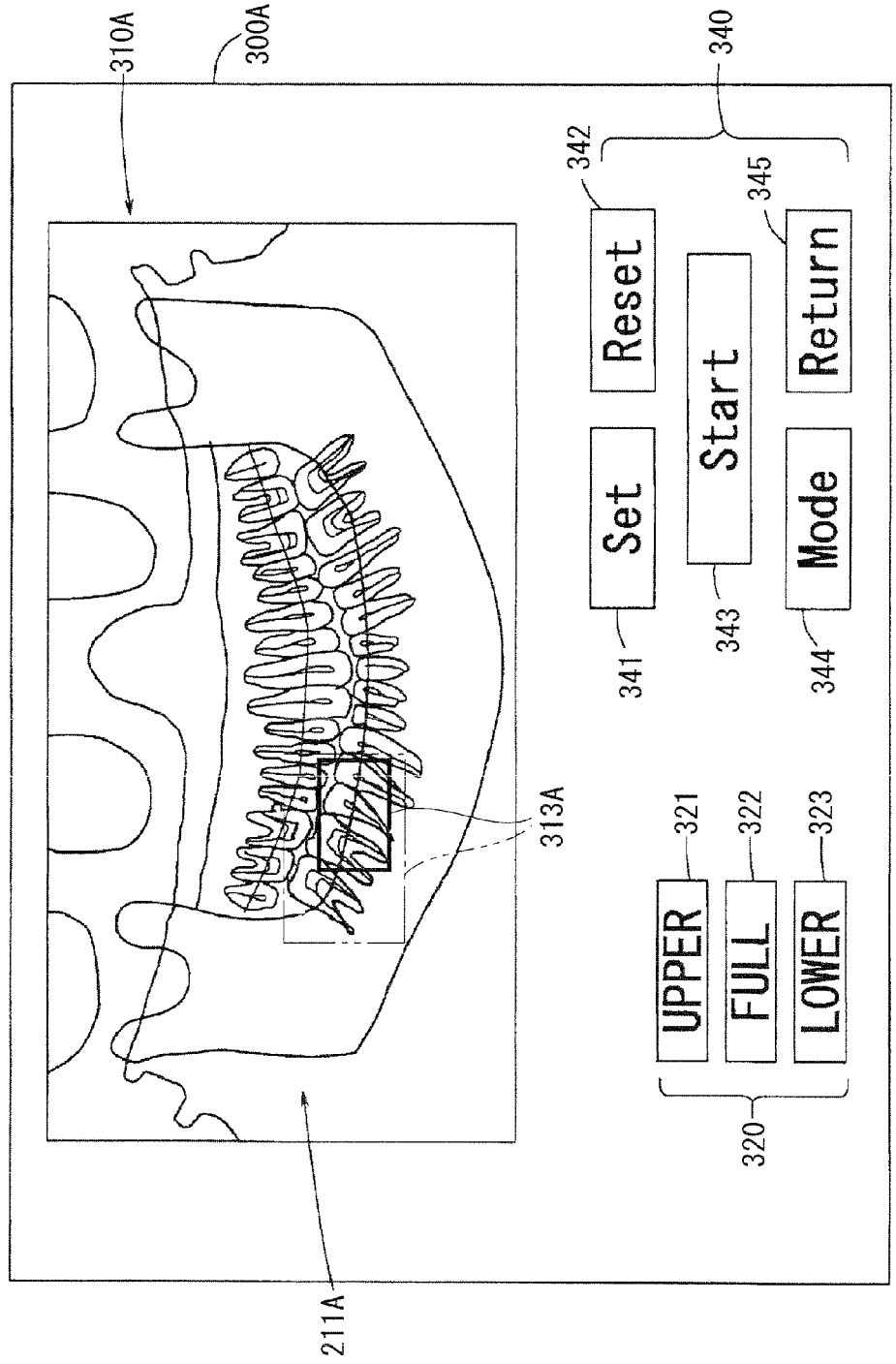

F I G . 2 1
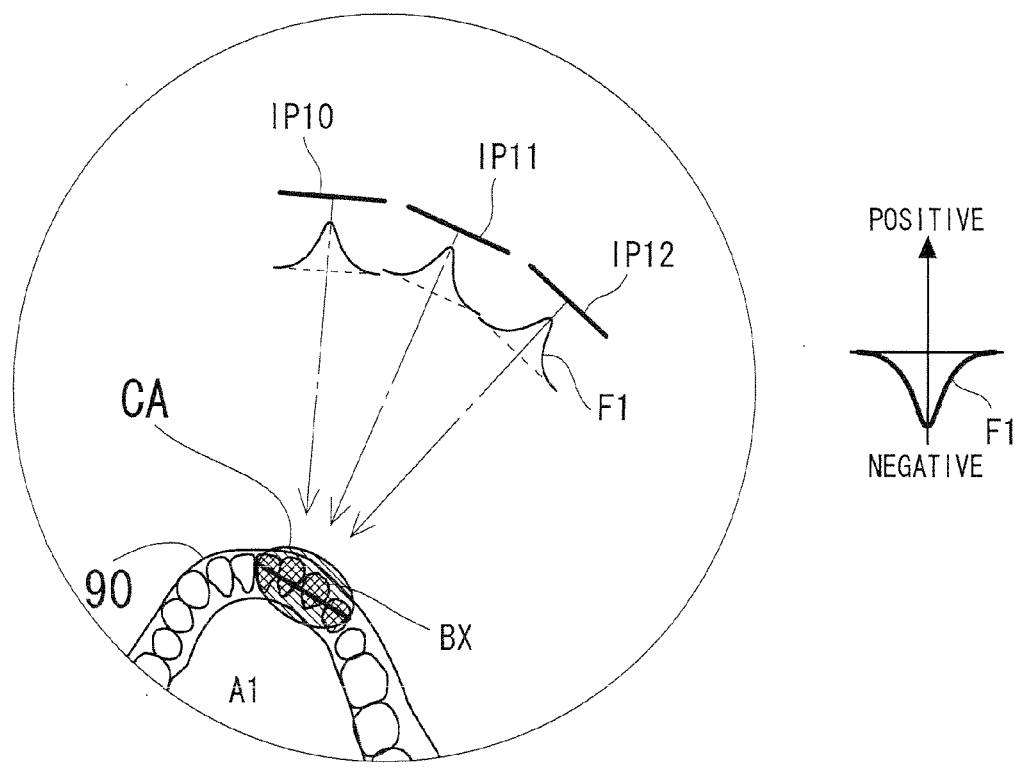

F I G . 2 2
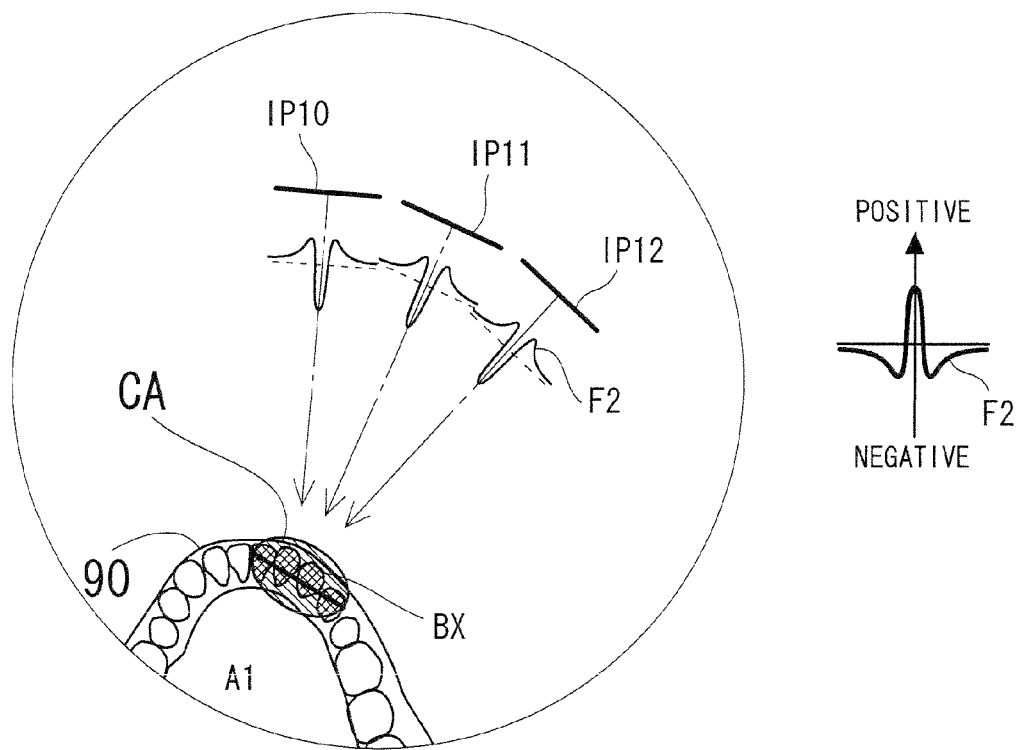

F I G . 2 6
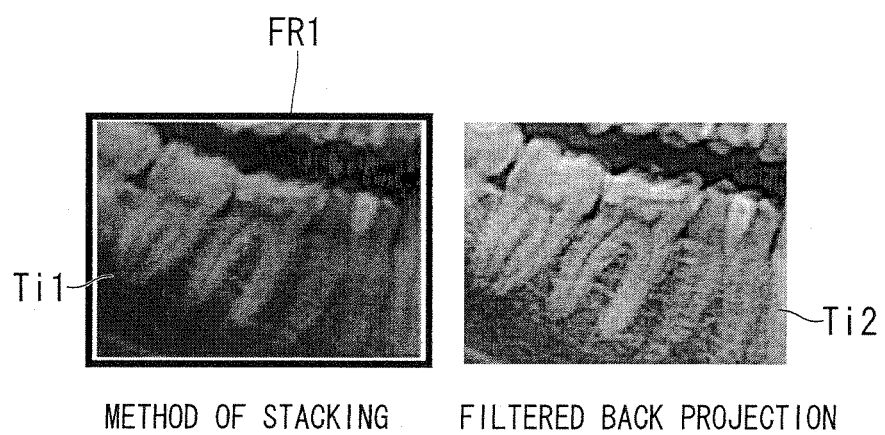

X-RAY PHOTOGRAPHY APPARATUS

BACKGROUND OF THE INVENTION

1. Field of the Invention

The present invention relates to an X-ray photography apparatus.

2. Description of the Background Art

Conventionally what is called intraoral radiography (dental radiography), in which X-ray a detection means (such as an X-ray film and an X-ray sensor panel) is set in the mouth cavity of a patient to photograph part of a row of teeth or a gum, is performed in X-ray photography of the dental field. Because only a local region is irradiated with an X-ray in the intraoral radiography, advantageously the photographing is simply performed and X-ray exposure is reduced. However, it is necessary to dispose in advance the X-ray detection means in the mouth cavity of the patient, and thus a large burden is placed on the patient.

Therefore, Japanese Patent Application Laid-Open No. 2007-136163 has made a proposal that panoramic photography is performed using a panoramic image photographing device and a tomographic image of part of the row of teeth or the gum is acquired using frame data obtained by the panoramic photography. In the panoramic photography, the X-ray is detected using an X-ray detector disposed outside the head of the patient. For this reason, the intraoral radiography can be performed in a pseudo manner while the burden on the patient is reduced.

For example, in the X-ray photography apparatus disclosed in Japanese Patent Application Laid-Open No. 2007-136163, a suitable gain (a shift amount in the case of shifting and adding frame data) is previously defined by a look-up table in each position of a region of interest. Therefore, the X-ray photography apparatus acquires the gain corresponding to the designated region of interest from the look-up table and, by shifting and adding the frame data according to the gain, generates one tomographic image. Therefore, in the conventional X-ray photography apparatus, only one type tomographic image is generated for a specific tomographic plane, and diagnostic information on part of the row of teeth or the gum is limited.

SUMMARY OF THE INVENTION

The present invention is directed to an X-ray photography apparatus.

In accordance with one aspect of the present invention, an X-ray photography apparatus of the present invention includes:

a support that supports an X-ray generator and an X-ray detector while the X-ray generator and the X-ray detector are opposed (or faced) to each other so that the head of a patent can be interposed therebetween, the X-ray detector outputting an electric signal according to the intensity of an incident X-ray;

a moving mechanism that includes a turning part and a moving part, the turning part relatively turning the X-ray generator and the X-ray detector about the head of the patient by turning the support relative to the head about a predetermined turning axis, and the moving part moving the support relative to the head in a direction perpendicular to the turning axis;

an image processor that generates a tomographic image related to a specific tomographic plane from a projection image of the X-ray based on the electric signal output from the X-ray detector;

a photographic region designation receiving part that receives an operation to designate a region including a row of teeth or part of a gum as a pseudo intraoral radiography region, the row of teeth or the gum being spread along the curve of a dental arch; and a controller that performs pseudo intraoral radiography to the pseudo intraoral radiography region in which designation is received by the photographic region designation receiving part, the X-ray generator irradiating the pseudo intraoral radiography region with the X-ray, the image processor performing different methods of image processing to X-ray image data obtained by the pseudo intraoral radiography, and generating plural tomographic images in which information contents related to X-ray absorption before and behind the specific tomographic plane differ from each other.

By generating the plural tomographic images having different information content related to X-ray absorption before and behind the tomographic plane, the plural tomographic images fitting in plural diagnostic purposes can be generated from pieces of data obtained by the identical X-ray photography, and multiple image diagnoses can be made. Additionally, the proper image diagnosis can be made by selecting the better tomographic image fitting in the diagnostic purpose from the plural tomographic images.

Preferably, the plural tomographic images include a tomographic image that is generated by a method of stacking a plurality of projection images and a tomographic image that is generated by a filtered back projection.

The tomographic image similar to the conventional intraoral radiography (the dental radiography) can be generated by superposing the plural projection images. In the tomographic image, because metallic artifact is not generated, the image diagnosis of the target place can properly be made. The tomographic image having an excellent contrast can be acquired by the filtered back projection. Therefore, the target place can be clearly observed to make the image diagnosis. Since the tomographic image generated by the method of stacking and the tomographic image generated by the filtered back projection are both generated, the image diagnosis can be properly made while shortcomings of both of the tomographic images are compensated.

Preferably, a convolution filter is used in the filtered back projection.

The information on the X-ray absorption of the site photographed before and behind the target cross-section can be reduced to obtain the clear tomographic image.

Preferably, the plural tomographic images include plural tomographic images, which are generated by the filtered back projection in which convolution filters different from each other are used.

The plural tomographic images having different information content on the X-ray absorption of the object located before and behind the target cutting plane can be obtained. Therefore, the better tomographic image fitting in the diagnosis can be selected.

Preferably, the irradiation range of an X-ray beam emitted from the X-ray generator includes a whole region of the pseudo intraoral radiography region.

The X-ray projection image having wealth of information on the X-ray absorption in the pseudo intraoral radiography region is obtained even if the support has a small turning angle.

Preferably, the X-ray photography apparatus of the present invention further includes an irradiation direction changing part that relatively changes the irradiation direction in which the head of the patient is irradiated with an X-ray emitted from the X-ray generator with respect to the axial direction of the body axis of the patient, wherein the irradiation direction changing part changes the irradiation direction according to the pseudo intraoral radiography region.

The X-ray irradiation can be performed at a fitting angle in each inclination of the tooth axis of the tooth. The tooth axis of the tooth varies in each site of the dental arch.

Preferably, the X-ray photography apparatus of the present invention further includes a display part that simultaneously or sequentially displays the plural tomographic images generated by the image processor.

The image diagnosis can be made by simultaneously or sequentially displaying the plural tomographic images generated by the image processor.

Preferably, the X-ray photography apparatus of the present invention further includes an image selector that receives an input operation to select a specific tomographic image from the plural tomographic images, wherein the display part highlights the specific tomographic image selected by the image selector compared with one or more residual tomographic images that are not selected.

By highlighting the selected specific tomographic image, a reader (or the operator of the apparatus) can make the image diagnosis while concentrating on the highlighted tomographic image.

Preferably, when highlighting the specific tomographic image, the display part performs at least one of the followings: (a) the one or more residual tomographic images are not displayed, (b) the specific tomographic image is displayed while enlarged compared with the one or more residual tomographic images, (c) the specific tomographic image is displayed on a previously-acquired panoramic image of a whole dental arch, and (d) a frame indicating the selection is displayed on the selected specific tomographic image.

The specific tomographic image can be displayed while being highlighted.

Preferably, the controller performs CT photography by turning the support about the turning axis relative to the head of the patient by at least 180 degrees.

The CT photography can be performed in addition to the pseudo intraoral radiography.

Preferably, the X-ray detector changes spatial resolution in detecting the X-ray between the pseudo intraoral radiography and the CT photography.

The X-ray photography can be performed with the spatial resolution suitable for each of the pseudo intraoral radiography and the CT photography.

Preferably, the photographic region designation receiving part displays a region designating image in order to designate a region where the CT photography is performed, and receives an input operation to the region designating image.

The CT photography region can easily be set.

Preferably, the controller moves the support relative to the head of the patient, irradiates the dental arch with an X-ray slit beam from the X-ray generator, and performs panoramic photography.

The panoramic photography can be performed in addition to the pseudo intraoral radiography.

Preferably, the X-ray detector changes spatial resolution in detecting the X-ray between the pseudo intraoral radiography and the CT photography.

The X-ray photography can be performed with the spatial resolution suitable for each of the pseudo intraoral radiography and the panoramic photography.

Preferably, the controller changes the magnification rate of an X-ray image so as to be acquired between the pseudo-intraoral radiography and the panoramic photography by changing the distance from the X-ray detector to the head of the patient.

The magnification rate can properly be changed between the pseudo intraoral radiography and the panoramic photography.

Preferably, the panoramic photography is a partial panoramic photography in which part of the region of the dental arch is set to a photography target.

The panoramic photography can be performed for part of the dental arch without the extra exposure of the subject to the X-rays.

Preferably, the photographic region designation receiving part displays a region designating image in order to designate the pseudo intraoral radiography region, and receives an input operation to the region designating image.

The pseudo intraoral radiography region can well be designated through the image.

Preferably, the region designating image is a panoramic image of the dental arch.

The pseudo intraoral radiography region can easily be designated through the panoramic image such that the photographing target object is included in the pseudo intraoral radiography region.

Preferably, the controller performs CT photography by turning the support about the turning axis relative to the head of the patient by at least 180 degrees, and the irradiation direction changing part changes the irradiation direction between the CT photography and the pseudo intraoral radiography.

The irradiation can be performed in a proper direction during the pseudo intraoral radiography and the CT photography.

Therefore, an object of the present invention is to provide a technology for enabling more diagnostic information on part of the row of teeth or the gum from the identical frame data.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a schematic perspective view of an X-ray photography apparatus according to a preferred embodiment of the present invention;

FIG. 3 is a block diagram of a configuration of the X-ray photography apparatus of the present invention;

FIGS. 6 and 7 are explanatory views of position adjustments of vertically-shielding plates and horizontally-shielding plates;

FIG. 10 is a view indicating a photography mode setting screen used to set a photography mode;

FIG. 11 is a view indicating a photographic region setting screen used to set a photographic region;

FIGS. 12 and 13 are views indicating other photographic region setting screens;

FIG. 21 is a view illustrating a filtered back projection to which a filter function is applied;

FIG. 22 is a view illustrating the filtered back projection to which another filter function is applied;

FIG. 26 is a view illustrating display examples of the tomographic image of the method of stacking and the tomographic image of the filtered back projection.

DESCRIPTION OF THE PREFERRED EMBODIMENTS

Figure 2:
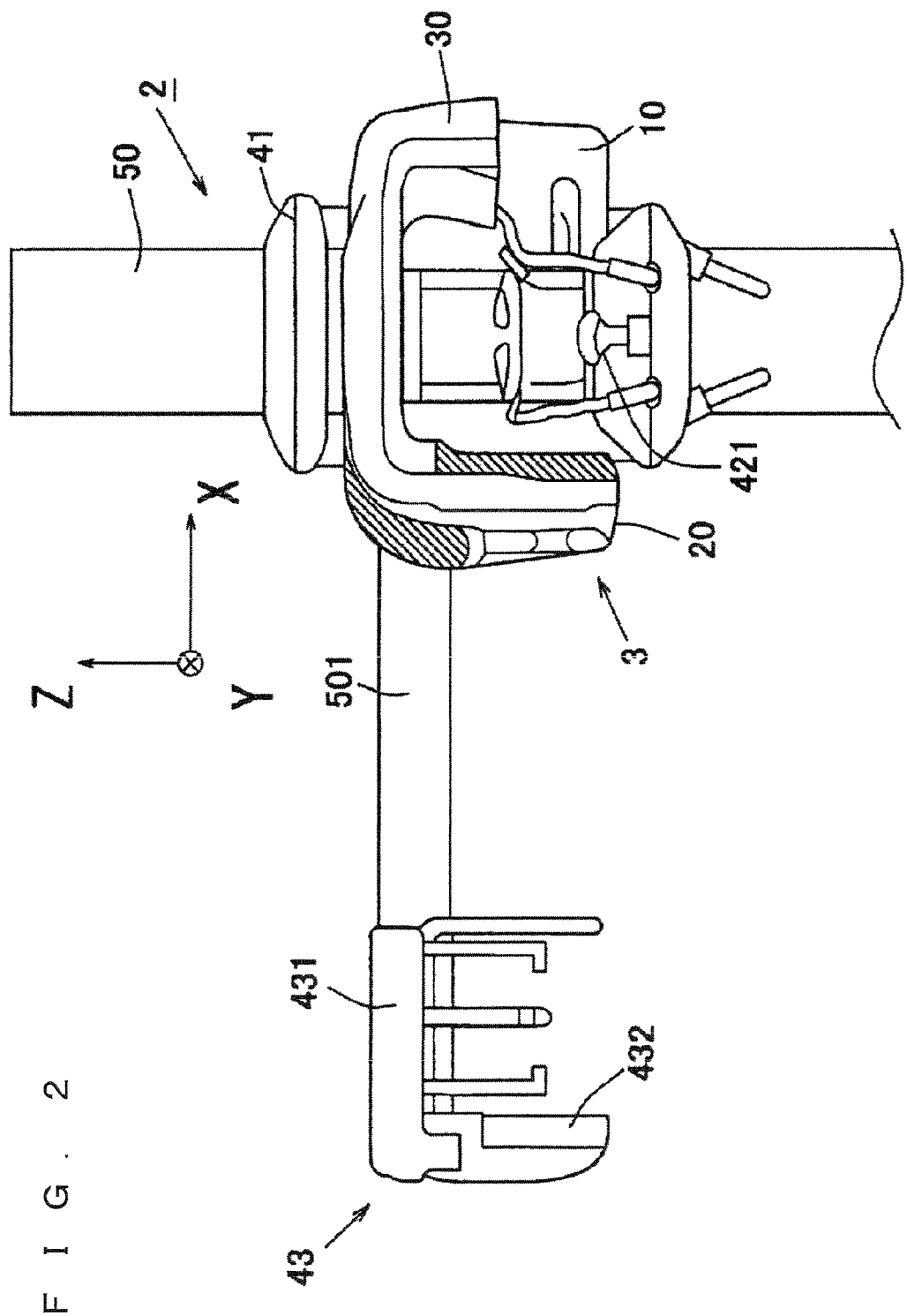
FIG. 2 is a partial front view of the X-ray photography apparatus on which a cephalostat is mounted.

Hereinafter, preferred embodiments of the present invention will be described with reference to the accompanying drawings. In the drawings, for the sake convenience, occasionally, the size or the number of pieces of each component is indicated while magnified or simplified as occasion demands.

FIG. 1 is a schematic perspective view of an X-ray photography apparatus 1 according to a preferred embodiment of the present invention. FIG. 2 is a partial front view of the X-ray photography apparatus 1 on which a cephalostat 43 is mounted. FIG. 3 is a block diagram of the configuration of the X-ray photography apparatus 1.

The X-ray photography apparatus 1 is substantially comprised of manipulation display parts 61 and 62, a main body 2, and an image processing device 8. The manipulation display parts 61 and 62 act as display element while setting a photographic region CA. The main body 2 collects X-ray projection data (frame data) by performing X-ray photography to the photographic region CA set through the manipulation display parts 61 and 62. The image processing device 8 generates various images by processing the projection data collected by the main body 2.

The main body controller 60 of the main body 2 and a controller, an image processor 801b, and a position setter 801c (see FIG. 3) of the image processing device 8 perform the X-ray photography according to a program IMP (not illustrated) of the X-ray photography.

Desirably the main body 2 is accommodated in a hollow, vertically long, cuboid-shape X-ray protective chamber 70 at a site of the X-ray photography. The main body 2, the manipulation display part 61 mounted on a wall surface of the X-ray protective chamber 70, and the image processing device 8 disposed outside the X-ray protective chamber 70 are connected to one another by a connection cable 83.

The main body 2 includes an X-ray generation part 10 and an X-ray detection part 20. The X-ray generation part 10 emits an X-ray beam BX (such as an X-ray cone beam BX1 and an X-ray slit beam (described later)) including a bundle of X-rays toward a subject M1. The X-ray detection part 20 detects the X-ray beam, which is transmitted through the subject M1 after emitted from the X-ray generation part 10. The main body 2 also includes a turning arm 30 serving as a support supporting the X-ray generation part 10 and the X-ray detection part 20, a vertically extending pillar 50, an elevating part 40 that can vertically be elevated with respect to the pillar 50 while suspending the turning arm 30, and a main body controller 60. The X-ray generation part 10, the X-ray detection part 20, and an X-ray beam forming mechanism 13 of the X-ray generation part 10 disposed on a side of the X-ray detection part 20 constitute a photographic mechanism 3.

The X-ray generation part 10 and the X-ray detection part 20 are suspended from and fixed to both end portions of a turning part 30c of the turning arm 30, respectively. The X-ray generation part 10 and the X-ray detection part 20 are supported so as to be opposed to each other. The turning arm 30 is suspended from the elevating part 40 with a vertically extending turning shaft 31 interposed therebetween.

The turning arm 30 has a substantially inverted U-shape when viewed from the front side. The turning arm 30 turns about the turning shaft 31 serving as a turning center Sc provided in the upper end portion of the turning part 30c. In the preferred embodiment, the elevating part 40 includes an upper frame 41 that extends frontward from the upper portion of the elevating part 40 when viewed from the front side, and the turning center Sc is fixed with respect to the upper frame 41.

The turning arm 30 of the preferred embodiment is formed in a U-shape. Alternatively, the turning arm 30 may be formed into different shapes. For example, an annular member that is rotatably fitted in the outer circumferential portion of a columnar-shaped member fixed above the subject M1 with, for example, a ball bearing and the like interposed therebetween may be used instead of the turning arm. In this case, the X-ray generation part 10 and the X-ray detection part 20 are attached to the annular member so as to be opposed to each other. The annular member rotates along the outer circumferential portion of the columnar-shaped member, which allows the X-ray generation part 10 and the X-ray detection part 20 to rotate about the head M10 of the subject M1 with the head M10 interposed therebetween.

Hereinafter, the direction (in the preferred embodiment, a vertical direction, namely, a longitudinal direction) parallel to the axial direction of the turning shaft 31 is referred to as a "Z-axis direction", the direction intersecting the Z-axis direction is referred to as an "X-axis direction", and the direction intersecting the X-axis direction and the Z-axis direction is referred to as a "Y-axis direction". The X-axis direction and the Y-axis direction may arbitrarily be defined. However, in the preferred embodiment, when a test person serving as the subject M1 is positioned in the X-ray photography apparatus 1 to directly face the pillar 50, the side-to-side direction of the test person is defined as the X-axis direction, and the front-back direction of the test person is defined as the Y-axis direction. In the preferred embodiment, it is assumed that the X-axis direction, the Y-axis direction, and the Z-axis direction are orthogonal to one another.

Hereinafter, occasionally, the Z-axis direction is referred to as a vertical direction, and the direction on a plane defined by a two-dimensional direction of the X-axis direction and the Y-axis direction is referred to as a horizontal direction.

On the other hand, as to three-dimensional coordinates on the turning arm 30, the direction in which the X-ray generation part 10 and the X-ray detection part 20 are opposed to each other is referred to as a "y-axis direction", the horizontal direction orthogonal to the y-axis direction is referred to as an "x-axis direction" and the vertical direction orthogonal to the x-axis direction and y-axis direction is referred to as a "z-axis direction". In the preferred embodiment and subsequent preferred embodiments, the z-axis direction and the Z-axis direction are parallel to each other. The turning arm 30 of the preferred embodiment turns about the vertically extending turning shaft 31 as a rotational axis (the turning axis). Accordingly, the xyz orthogonal coordinate system rotates about the Z-axis (=the z-axis) with respect to the XYZ orthogonal coordinate system.

In the preferred embodiment, as indicated in FIG. 1, when the test person faces the pillar 50, the right-hand direction is referred to as a (+X)-direction, the back-side direction is referred to as a (+Y)-direction, and the upwardly vertical direction is referred to as a (+Z)-direction. When the X-ray generation part 10 and the X-ray detection part 20 are viewed from above in plan, the direction from the X-ray generation part 10 toward the X-ray detection part 20 is referred to as a +y-direction, the left-hand direction from a −y-side toward the +y-direction is referred to as a +x-direction, and the upwardly vertical direction is referred to as a +z-direction.

The elevating part 40 includes the upper frame 41 (a first support retention part) and a lower frame 42, and engages the vertically-provided pillar 50 provided. The turning shaft 31 is attached to the upper frame 41 that acts as a retention part for the support. The elevating part 40 moves vertically along the pillar 50, whereby the turning arm 30 moves up and down.

As to the structure that turns the turning arm 30, the turning arm 30 may be provided so as to be turnable with respect to the turning shaft 31 attached to the upper frame 41 so as to be non-turnable, and the turning arm 30 may turn with respect to the turning shaft 31. Alternatively, the turning arm 30 may be fixed so as to be non-turnable with respect to the turning shaft 31 provided to the upper frame 41 so as to be turnable, and the turning arm 30 may turn by turning the turning shaft 31.

In the structure that turns the turning arm 30, the torque of a turning motor (a support turning drive part) can act on the turning arm 30 through a power transmission mechanism (not illustrated) such as a belt and a pulley. For example, the turning motor is fixed to the inside of the turning arm 30, and an annular belt is entrained about the pulley fixed to the rotational shaft of the turning motor and the turning shaft 31 such that the torque of the turning motor acts on the turning arm 30. In this case, a bearing member such as a bearing may be interposed between the turning shaft 31 and the turning arm 30.

Alternatively, a turning motor that turns the turning arm 30 about the turning shaft 31 may be provided in the upper frame 41, and the transmission mechanism (not illustrated), which includes a belt, a pulley, and a rotational shaft and passes through the turning shaft 31, may transmit the torque of the turning motor to the turning arm 30 to turn the turning arm 30.

In the structure in which the turning arm 30 is fixed so as to be non-turnable, the turning arm 30 is unturnably fixed to the turning shaft 31 turnable with respect to the upper frame 41, and the turning arm 30 may turn by turning the turning shaft 31 as a matter of course. In this structure, the turning motor is fixed to the inside of the upper frame 41, and the torque of the turning motor can act on the rotation of the turning shaft 31 using the transmission mechanism (not illustrated) such as a roller. In this case, a bearing member such as a ball bearing may be interposed between the turning shaft 31 and upper frame 41.

In the preferred embodiment, the turning shaft 31 is configured to extend vertically. Alternatively, it is also conceivable that the turning shaft 31 is obliquely disposed at any angle with respect to the vertical direction.

The bearing (not illustrated) is interposed between the turning shaft 31 and the turning arm 30. Therefore, the turning arm 30 can rotate smoothly with respect to the turning shaft 31. The turning shaft 31, the transmission mechanism including the bearing, the belt, the pulley, and the rotational shaft, and the turning motor are an example of a revolving part 201 (see FIG. 3) that turns the turning arm 30. In other words, the revolving part 201 relatively turns the turning arm 30 (the support) about the turning shaft 31 with respect to the head M10 of the subject M1. Therefore, the revolving part 201 relatively turns an X-ray generator 10a and an X-ray detector 21 about the head M10 of the subject M1.

In the preferred embodiment, the turning arm 30 turns with respect to the turning shaft 31, which is located at a fixed position so as not to rotate. However, as described above, it is also conceivable that the turning shaft 31 fixed to the turning arm 30 is turned with respect to upper frame 41 to turn the turning arm 30. In this case, the bearing that rotatably supports the turning shaft 31 is formed in the upper frame 41.

The main body 2 includes a moving part 202 that relatively moves the turning arm 30 in the direction (the X-direction or the Y-direction) perpendicular to the turning shaft with respect to the head M10 of the subject M1. The moving part 202 can be constructed by an XY table (not illustrated), which is fixed to the upper frame 41 or the turning arm 30. The XY table includes a table member that moves in the X-axis direction, a table member that moves in the Y-axis direction, and a motor that moves the table members in the X-axis direction and the Y-axis direction. In the case that the XY table is fixed to the upper frame 41, the XY table is fixed to the upper end portion of the turning shaft 31. In this case, by driving the XY table, the turning arm 30 moves in the direction perpendicular to the turning shaft 31 together with the turning shaft 31. In the case that the XY table is fixed to the turning arm 30, the XY table is fixed to the lower end portion of the turning shaft 31. In this case, only the turning arm 30 moves in the direction perpendicular to the turning shaft 31.

Using the XY table, the turning center of the X-ray generator 10a and the X-ray detector 21 can be fixed to a place different from the turning shaft 31 serving as the mechanical turning axis.

For example, in CT photography, the center of the photographic region CA is set on the line connecting the centers of the X-ray generator 10a and the X-ray detector 21 when the X-ray generator 10a, the X-ray detector 21, and the photographic region CA is looked down in the Z-direction. The axis center of the turning shaft 31 is set to a place different from the photographic region CA on the line connecting the centers of the X-ray generator 10a and the X-ray detector 21. Under this geometric condition, the turning arm 30 is turned about the turning shaft 31, and the XY table turns the turning shaft 31 about the center of the photographic region CA by an angle equal to the turning angle of the turning arm 30. In this manner, the CT photography can be performed by irradiating the photographic region CA with the X-ray cone beam while the X-ray generator 10a and the X-ray detector 21 turn about the center of the photographic region CA.

Japanese Patent Application Laid-Open No. 2007-29168 and International Patent Publication No. 2009/063974, which have been filed by the applicant of the present application, disclose the configuration implementing the above CT photography, and can also be appropriately applied to the present invention.

In the preferred embodiment of the present application, a moving mechanism 200 including the revolving part 201 and the moving part 202 can relatively move the turning arm 30 with respect to the head M10 of the subject M1. However, the moving mechanism 200 is not limited to the above configuration. For example, the main body 2 may be configured such that the moving mechanism 200 rotates the subject M1 about a predetermined rotational axis, or such that the moving mechanism 200 moves the subject M1 in the direction perpendicular to the rotational axis.

A subject retention part 421 is provided in the lower frame 42. The subject retention part 421 includes an ear rod that fixes the head M10 of the subject M1 of a human body from the right and left sides and a chin rest that fixes the chin of the patient.

The turning arm 30 is disposed at a proper position by elevating the elevating part 40 according to the height of the subject M1. At this point, the subject M1 is fixed to the subject retention part 421. In the example illustrated in FIG. 1, the subject retention part 421 retains the subject M1 such that the body axis MX1 of the subject M1 is substantially aligned with the axial direction of the turning shaft 31. As used herein, the "body axis" means a symmetrical axis, which is set in the case that the human body is considered to be substantially symmetrical when viewed from the front side.

A support driving controller 602 (see FIG. 3) of the main body controller 60 controls the operations of the elevating part 40 and the moving mechanism 200.

The main body controller 60 is a controller that controls the operation of each component of the main body 2. For example, the main body controller 60 acts as an X-ray regulating controller and a drive controller. As indicated in FIG. 1, the main body controller 60 is disposed inside the X-ray detection part 20.

A manipulation display part 62 is attached to the outside of the main body controller 60, namely, on the +y side of the X-ray detection part 20. The manipulation display part 62 includes buttons that are used to input various designation or a touch panel that displays various pieces of information.

The manipulation display part 61 is attached to the outside of the wall of the X-ray protective chamber 70 that accommodates the main body 2 therein. The manipulation display part 61 is connected to the main body controller 60, and includes buttons that are used to input various designations and a touch panel that displays various pieces of information.

An operator (for example, a practitioner) may manipulate the main body 2 using the manipulation display part 62, or manipulate the main body 2 using the manipulation display part 61. The manipulation display part 62 may differ from the manipulation display part 61 in a manipulation content or a display content. Part or whole of the manipulation content or display content may be common to the manipulation display part 62 and the manipulation display part 61.

In the case that the X-ray protective chamber 70 is eliminated, the manipulation display part 61 may be eliminated as well. One of the manipulation display part 62 and the manipulation display part 61 may be eliminated. Although the display and manipulation performed through the manipulation display part 61 are described below, the display and manipulation performed through the manipulation display part 61 may be replaced with the display and manipulation performed through the manipulation display part 62.

The manipulation display part 61 is also used, for example, to designate the position of the photographic region of a biological organ. There are various modes in the X-ray photography, and the mode may be selected by the manipulation of the manipulation display part 61.

The image processing device 8 includes an image processing main body 80, a display part 81 including a display device such as a liquid crystal monitor, and a manipulation part 82 including a keyboard and a mouse. The operator (the practitioner) can input various commands to the image processing device 8 through the manipulation part 82. The display part 81 may include the touch panel. In this case, the display part 81 may include part of or whole of the functions of the manipulation part 82.

For example, the image processing main body 80 includes a computer or a workstation. The image processing main body 80 transmits and receives various pieces of data to and from the main body 2 through the connection cable 83 serving as the communication cable. Alternatively, the main body 2 and the image processing main body 80 may wirelessly conduct data communication with each other.

For example, the image processing device 8 processes the projection data acquired by the main body 2, and reconstructs three-dimensional data (volume data) expressed in the voxel form. For example, a specific cutting plane can be set to the three-dimensional data, and a tomographic image is reconstructed in the specific cutting plane.

It is also considered that the X-ray photography apparatus 1 is used as an apparatus that collects only the frame data by the X-ray photography. In such cases, the image processing device 8 may be eliminated.

As indicated in FIG. 2, the cephalostat 43 may be attached to the X-ray photography apparatus 1. For example, the cephalostat 43 is attached to an arm 501 that extends horizontally from the middle of the elevating part 40. The cephalostat 43 includes a fixture 431 that fixes the head M10 to a given position and an X-ray detector 432 for cephalic photography. For example, a cephalostat disclosed in Japanese Patent Application Laid-Open No. 2003-245277 or a cephalostat similar thereto can be used as the cephalostat 43.

<Irradiation Direction Changing Part>

Figure 4:
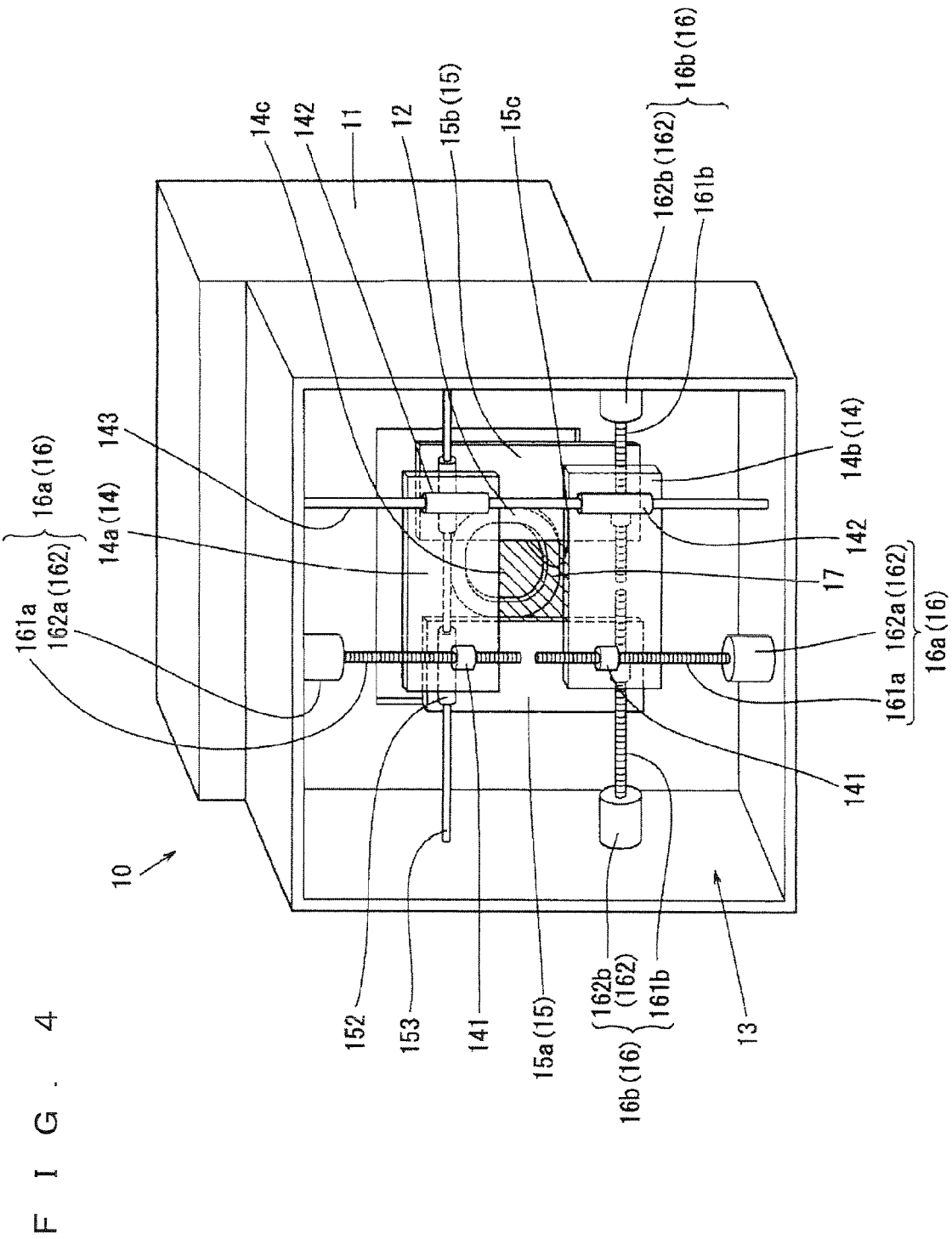
FIG. 4 is a schematic perspective view of an X-ray beam forming mechanism (an X-ray regulating part) of the X-ray photography apparatus of the present invention.
Figure 5:
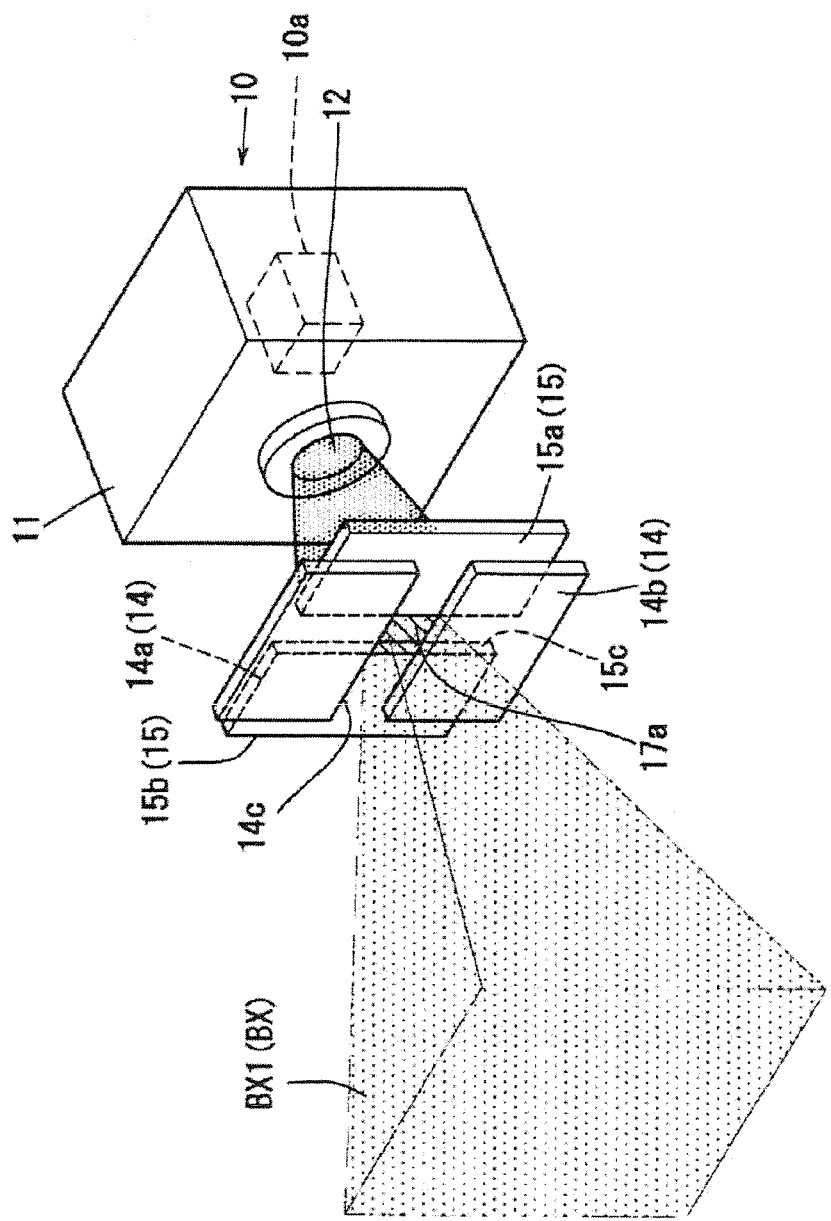
FIG. 5 is a schematic perspective view of an X-ray generation part of the X-ray photography apparatus that emits an X-ray cone beam in which an irradiation range is regulated.
Figure 7:
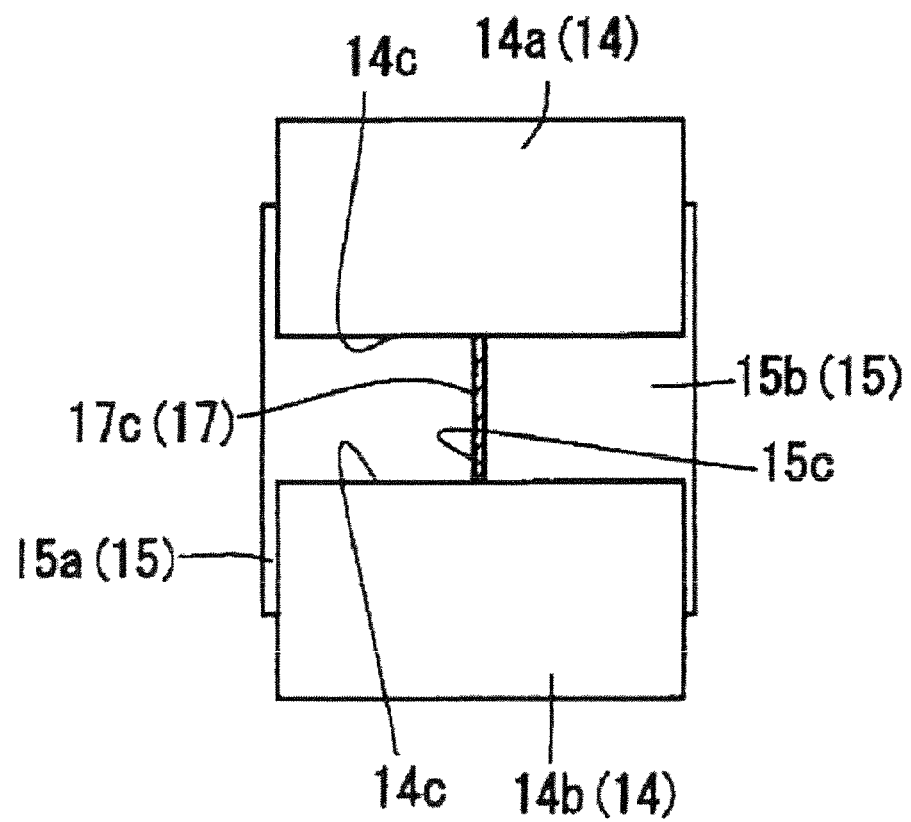
Figure 8:
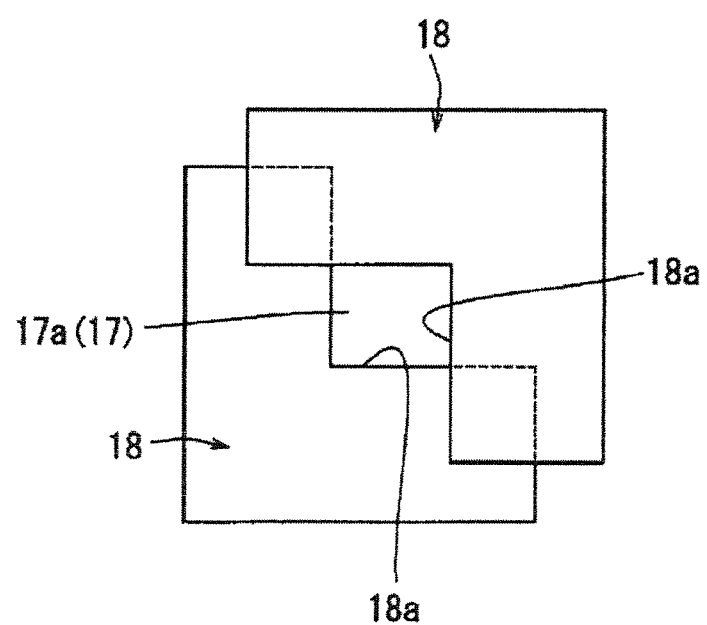
FIGS. 8 and 9 are explanatory views of the position adjustments of two L-shape shielding plates.
Figure 9:
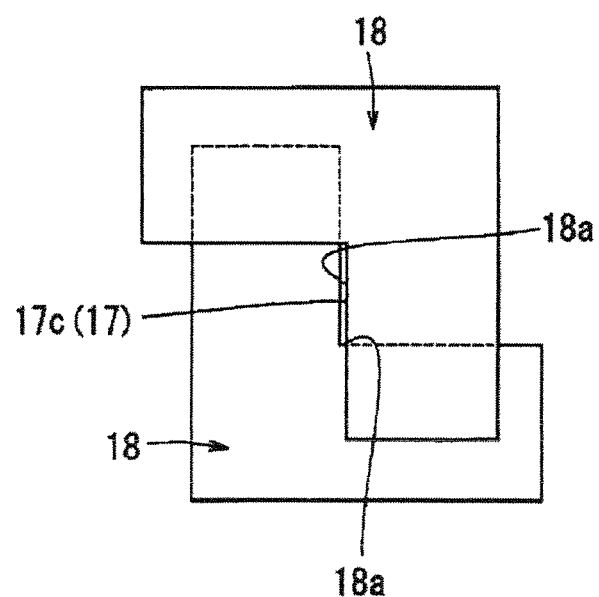

FIG. 4 is a schematic perspective view of the X-ray beam forming mechanism 13 (the X-ray regulating part). FIG. 5 is a schematic perspective view of the X-ray generation part 10 that emits the X-ray cone beam BX1 in which an irradiation range is regulated. FIGS. 6 and 7 are explanatory views of position adjustments of the vertically-shielding plates 14 and the horizontally-shielding plates 15. FIGS. 8 and 9 are explanatory views of the position adjustments of two L-shape shielding plates 18 and 18.

In the turning arm 30, the X-ray generation part 10 that is disposed so as to be opposed to the X-ray detection part 20 includes the X-ray generator 10a including an X-ray tube accommodated in a housing 11 (see FIG. 3). An outgoing port 12 that permits transmission of the X-ray generated by the X-ray tube is provided in the front surface of the housing 11. The X-ray beam forming mechanism 13 that acts as the X-ray regulating part is disposed in front of the outgoing port 12. In other words, the X-ray beam forming mechanism 13 is disposed on the front side of the outgoing port 12 in FIG. 4 and the side of the −y-direction in the Y-axis direction with respect to the X-ray generation part 10.

The X-ray beam forming mechanism 13 includes vertically-shielding plates 14 that move in the vertical direction (the Z-axis direction) to shield the X-ray irradiation direction, horizontally-shielding plates 15 that move in the horizontal direction (the X-axis direction) to shield the X-ray irradiation direction, and a shielding plate moving mechanism 16 that moves the vertically-shielding plates 14 and the horizontally-shielding plates 15. The shielding plate moving mechanism 16 is an example of an X-ray-regulating-part drive part illustrated in FIG. 3. An X-ray-regulating-part drive controller 605 of the main body controller 60 controls the drive of the X-ray beam forming mechanism 13 (specifically, the shielding plate moving mechanism 16). The vertically-shielding plates 14 and the horizontally-shielding plates 15 are examples of the X-ray shielding member that is used to regulate a shield amount of the X-ray generated from the X-ray generator 10a in a limited manner.

The vertically-shielding plate 14s includes a horizontally-long upper vertically-shielding plate 14a and a horizontally-long lower vertically-shielding plate 14b, which are disposed above and below (the +z side and the −z side) the outgoing port 12 when viewed from the front side. The horizontally-shielding plates 15 includes a vertically-long left horizontally-shielding plate 15a and a vertically-long right horizontally-shielding plate 15b, which are disposed on the right and left sides (the −x side and the +x side) of the outgoing port 12 when viewed from the front side. In the example illustrated in FIG. 4, the horizontally-shielding plates 15 are disposed on the side (the −y side) of the housing 11 of the vertically-shielding plates 14. Alternatively, the vertically-shielding plates 14 may be disposed on the side of the housing 11 of the horizontally-shielding plates 15.

The shielding plate moving mechanism 16 includes a pair of shielding-plate vertically-moving mechanisms 16a that move the upper vertically-shielding plate 14a and the lower vertically-shielding plate 14b in the vertically-direction and a pair of shielding-plate horizontally-moving mechanisms 16b that move the left horizontally-shielding plate 15a and the right horizontally-shielding plate 15b in the horizontal direction.

The shielding-plate vertically-moving mechanism 16a includes nut members 141 that are attached to the upper vertically-shielding plate 14a and the lower vertically-shielding plate 14b, vertical screw shafts 161a that extend vertically to engage the nut members 141, and position adjustment motors 162a (162) that normally or reversely rotate the screw shafts 161a. The screw shaft 161a is normally or reversely rotated by driving the position adjustment motor 162a, whereby the nut member 141 moves up and down along the vertical direction. Therefore, the upper vertically-shielding plate 14a and the lower vertically-shielding plate 14b move independently in the vertical direction. Under the control of the main body controller 60 (specifically, the X-ray-regulating-part drive controller 605), the shielding-plate vertically-moving mechanism 16a adjusts the vertical shielding amount of the X-ray beam emitted from the X-ray generator 10a using the upper vertically-shielding plate 14a and the lower vertically-shielding plate 14b. The shielding-plate vertically-moving mechanism 16a is an example of a first elevating mechanism, which controls the irradiation direction (a direction in which the center line of an irradiation range extends) by adjusting the spreading (the irradiation range) of the X-ray beam related to the vertical direction, namely, the direction related to the axial direction of the turning shaft 31.

A regulating cylindrical body 142 is attached to each of the upper vertically-shielding plate 14a and the lower vertically-shielding plate 14b. A through-hole is made in the regulating cylindrical body 142 so as to vertically pierce the regulating cylindrical body 142. A vertically extending regulating shaft 143 is fitted in the regulating cylindrical body 142, and the vertical movement of the regulating cylindrical body 142 is regulated by the regulating shaft 143. Therefore, the upper vertically-shielding plate 14a and the lower vertically-shielding plate 14b move vertically with little or no inclination.

The shielding-plate horizontally-moving mechanism 16b includes nut members 161 that are attached respectively to the left horizontally-shielding plate 15a and the right horizontally-shielding plate 15b, vertical screw shafts 161b that extend vertically to engage the nut members 161, and position adjustment motors 162b (162) that normally or reversely rotate the screw shafts 161b. The screw shaft 161b is normally or reversely rotated by driving the position adjustment motor 162b, whereby the nut member 161 moves right and left in the horizontal direction. Therefore, the left horizontally-shielding plate 15a and the right horizontally-shielding plate 15b move independently in the horizontal direction. Under the control of the main body controller 60, the shielding-plate horizontally-moving mechanism 16b adjusts the horizontal shielding amount of the X-ray beam emitted from the X-ray generator 10a using the left horizontally-shielding plate 15a and the right horizontally-shielding plate 15b. The shielding-plate horizontally-moving mechanism 16b is an example of the horizontal irradiation position controller, which controls the irradiation direction by adjusting the irradiation range related to the horizontal direction of the X-ray beam.

A regulating cylindrical body 152 is attached to each of the left horizontally-shielding plate 15a and the right horizontally-shielding plate 15b. A through-hole is made in the regulating cylindrical body 152 so as to pierce the regulating cylindrical body 152 in the horizontal direction. A regulating shaft 153 extending horizontally is fitted in the regulating cylindrical body 152, and the horizontal movement of the regulating cylindrical body 152 is regulated by the regulating shaft 153. Therefore, the left horizontally-shielding plate 15a and the horizontally-shielding plate 15b move horizontally with little or no inclination.

In the preferred embodiment, the X-ray beam forming mechanism 13 includes the vertically-shielding plates 14, the horizontally-shielding plates 15, and the shielding plate moving mechanism 16, and the X-ray beam forming mechanism 13 is disposed in front of the outgoing port 12 of the X-ray generation part 10. Therefore, the irradiation range of the X-ray generated by the X-ray generation part 10 is regulated by the shielding to form the X-ray cone beam BX1 that spreads in a truncated pyramid shape toward the X-ray detection part 20 (see FIG. 5).

Particularly, an interval between opposing edge portions 14c and 14c in the upper vertically-shielding plate 14a and the lower vertically-shielding plate 14b is adjusted by the shielding-plate vertically-moving mechanism 16a, and an interval between opposing edge portions 15c and 15c in the left horizontally-shielding plate 15a and the right horizontally-shielding plate 15b is adjusted by the shielding-plate horizontally-moving mechanism 16b. In order to form a desired-shape X-ray cone beam BX1, an opening 17 that has a quadrangular shape when viewed from the front side is formed by the opposing edge portions 14c and 14c and the opposing edge portions 15c and 15c.

For example, as indicated in FIG. 6, the interval between the opposing edge portions 14c and 14c is widely adjusted, and the interval between the opposing edge portions 15c and 15c is widely adjusted, whereby the opening 17 becomes a relatively large square opening 17a for large irradiation field when viewed from the front side. The X-ray passing through the opening 17a for large irradiation field has a square section, and becomes the X-ray cone beam BX1 that spreads in the square truncated pyramid shape toward the X-ray detection part 20.

As indicated in FIG. 7, the interval between the opposing edge portions 14c and 14c is widely adjusted, and the interval between the opposing edge portions 15c and 15c is narrowly adjusted, whereby the opening 17 becomes a rectangular, panoramic-photography opening 17c that is vertically long when viewed from the front side. The X-ray transmitted through the panoramic photography opening 17c becomes the X-ray slit beam that spreads in the vertically long truncated pyramid shape toward the X-ray detection part 20.

As illustrated in FIGS. 8 and 9, the X-ray beam forming mechanism may be constructed by two L-shape shielding plates 18 and 18, which have an L-shape when viewed from the front side and are symmetrically disposed with respect to the center of the opening 17. In this case, the opening 17 is constructed by edge portions 18a and 18a constituting internal angle portions of the two L-shape shielding plates 18 and 18.

For example, the shielding-plate vertically-moving mechanism 16a and the shielding-plate horizontally-moving mechanism 16b are provided, and the L-shape shielding plates 18 and 18 are moved in the vertical direction and the horizontal direction, which allows the shape of the opening 17 to be adjusted.

For example, a vertically-moving mechanism similar to the shielding-plate vertically-moving mechanism 16a is provided on a base (not illustrated) that is displaced horizontally by a horizontally-moving mechanism similar to the shielding-plate horizontally-moving mechanism 16b, and the one L-shape shielding plate 18 is vertically displaced by the vertically-moving mechanism. Each L-shape shielding plate 18 can be moved in the vertical direction and the horizontal direction by the horizontally-moving mechanism, the base, and the vertical moving mechanism. For example, the X-ray cone beam BX1 can be formed by widening the opening 17 as indicated in FIG. 8, and the X-ray slit beam can be formed by making the opening 17 narrow as indicated in FIG. 9.

<Photography Mode Selection Screen>

FIG. 10 is a view illustrating a photography mode setting screen MSW used to set a photography mode. The photography mode setting screen MSW indicated in FIG. 10 includes a pseudo intraoral radiography mode button FIM, a panoramic photography mode button PM, a CT photography mode button CM, and a cephalic photography mode button SM. The pseudo intraoral radiography mode button FIM is used to select a pseudo intraoral radiography mode. The panoramic photography mode button is used to select a panoramic photography mode. The CT photography mode button CM is used to select a CT photography mode. The cephalic photography mode button is used to select a cephalic photography mode.

For example, the photography mode selection screen MSW is displayed on the manipulation display part 61 or the manipulation display part 62 before the photographing is performed after the X-ray photography apparatus 1 is started up. The operator selects a desired photography mode through the photography mode selection screen MSW. A mode setter 601 (see FIG. 3) of the main body controller 60 sets the photography mode of the main body controller 60 to the selected photography mode. Therefore, in the X-ray photography apparatus 1, a photographing condition (such as the position and the shape of the photographic region) can be set according to the X-ray photography of the set type. Thus, the manipulation display part 61 or the manipulation display part 62 acts as the mode selector. The photography mode setting screen MSW is displayed on the display part 81 of the image processing device 8, and the mode may be selected through the manipulation part 82.

The pseudo intraoral radiography mode is one in which the pseudo intraoral radiography is performed. In the pseudo intraoral radiography, the conventional intraoral radiography (the dental radiography) is performed in the pseudo manner with the X-ray photography apparatus 1 while the partial region (for example, several teeth) of the row of teeth extending along the dental arch or part of the gum is set to the photographing target. At this point, the X-ray image obtained by the conventional intraoral radiography is a simple projection image, which is obtained by irradiating the partial region of the row of teeth or gum with the X-ray in one direction while the conventional X-ray film is set in the mouth cavity. On the other hand, in the pseudo intraoral radiography, the image equivalent to the simple projection image can be acquired as the tomographic image.

In the conventional intraoral radiography, the conventional X-ray film (or imaging plate and so on) put inside mouth oral cavity receives the X-ray passed through the target teeth or tooth, so the X-ray which passed through only the target teeth or tooth should be detected. In contrast, the pseudo intraoral radiography of the present invention is executed by way of extraoral radiograph, so the X-ray which passed through the hard tissue other than the target teeth or tooth is also detected. In the present invention, the projection images are processed into tomographic image in order to avoid image formation of the image data other than the target teeth or tooth as much as possible. In other words, the pseudo intraoral radiography of the present invention is a radiography which executes X-ray radiography of the imaging region equivalent to the imaging region of conventional intraoral radiography by extraoral radiography in the way of tomography.

More specifically, the X-ray cone beam BX1 in which the irradiation range is regulated so as to include the whole photographic region (a pseudo intraoral radiography region) is formed in the pseudo intraoral radiography. The photographic region is irradiated with the X-ray cone beam BX1 in plural directions (the directions within a predetermined range) to obtain the frame data. The image processor 801b of the image processing device 8 applies a method of stacking (shift-and-add method) (described later) to the obtained frame data to perform stacking of the X-ray projection images expressed by the frame data, thereby generating the tomographic image of the specific cutting plane. Although the tomographic image generated in this manner differs strictly from the X-ray image obtained by the conventional intraoral radiography in characteristic, the tomographic image is extremely similar to the X-ray image obtained by the conventional intraoral radiography from the viewpoint of the image diagnosis.

The image processor 801b applies a filtered back projection (described later) to the obtained frame data to generate the tomographic image of the specific cutting plane. Thus, the image processor 801b processes the frame data (X-ray projection image data) acquired by the pseudo intraoral radiography by image processing methods different from each other, namely, the method of stacking and the filtered back projection.

The position setter 801c of the image processing device 8 indicated in FIG. 3 mainly perform coordinate calculation to identify the position of the cutting plane, when the position of the cutting plane is set or when the position of the cutting plane is changed. The image processor 801b generates the tomographic image based on the coordinates of the cutting plane identified by the position setter 801c.

The panoramic photography mode is one in which the panoramic photography (panoramic X-ray photography) is performed. In the panoramic photography, the row of teeth is irradiated along a dental arch with the X-ray beam formed into the X-ray slit beam, thereby obtaining the frame data. The image processing device 8 (the image processor 801*b*) generates one panoramic image (a panoramic X-ray image) by connecting the end portions of the projection images expressed by the frame data.

The CT photography mode is one in which the CT photography is performed. In the CT photography, the X-ray cone beam BX1 is formed in which the irradiation range is regulated so as to include the whole photographic region (the CT photographic region). The turning arm 30 turns relatively at least 180 degrees with respect to the head M10. The photographic region is irradiated with the X-ray cone beam BX1 in multiple directions (for example, the directions of at least 180 degrees) to acquire the frame data expressing the X-ray projection image. The image processing device 8 (specifically, the image processor 801*b*) reconstructs the tomographic image of the specific cutting plane by applying the filtered back projection to the obtained frame data.

The cephalic photography mode is one in which the cephalic photography is performed. In the cephalic photography, as indicated in FIG. 2, the cephalostat 43 is mounted on the X-ray photography apparatus 1, and the head M10 of the test subject is irradiated with the X-ray slit beam formed for the purpose of the cephalic photography to obtain the frame data. The image processing device 8 (specifically, the image processor 801*b*) generates the projection image (a head X-ray standard photograph) of the entire head M10 by connecting the end portions of the projection images expressed by the frame data.

<Photographic Region Setting Screen>

FIG. 11 is a view indicating a photographic region setting screen 300 used to set the photographic region CA. The photographic region setting screen 300 indicated in FIG. 11 includes an image display portion 310, an upper and lower jaw selection portion 320, a selection range setting portion 330, and a condition setting portion 340. The condition setting portion 340 includes a set button 341, a reset button 342, a start button 343, a mode button 344, and a return button 345.

A dental arch image 211, a designation cursor 312, and a true-circle-like photographic region line 313 are displayed in the image display portion 310 while superposed on each other. The designation cursor 312 designates each point. The photographic region line 313 has the center designated by the designation cursor 312, and a radius designated by the selection range setting portion 330 (described later). The dental arch image 211 is a schematic diagram in which a plan view of the row of teeth having a standard size is schematically drawn. The dental arch image 211 is an example of the region designating image.

The upper and lower jaw selection portion 320 includes an UPPER button 321 for setting the photographic region CA to the upper jaw, a FULL button 322 for setting the photographic region CA to the upper jaw and lower jaw, and a LOWER button 323 for setting the photographic region CA to the lower jaw. For example, by the selection through the upper and lower jaw selection portion 320, the photography mode of the main body 2 is set to one of a CT photography mode (a first CT photography mode) in which the region extending across the upper jaw and the lower jaw is set to the target region of the CT photography and a CT photography mode (a second CT photography mode) in which one of the regions of the upper jaw and the lower jaw is set to the target region of the CT photography.

The condition setting portion 340 is constructed by the set button 341, the reset button 342, the start button 343, the mode button 344, and the return button 345. The set button 341 is manipulated to determine a designation content of the photographic region CA. The designation content of the photographic region CA is set through the image display portion 310, the upper and lower jaw selection portion 320, and the selection range setting portion 330. The reset button 342 is manipulated when the designation content of the photographic region CA, which is set through the image display portion 310, the upper and lower jaw selection portion 320, and the selection range setting portion 330.

The start button 343 is manipulated to provide an instruction to start the photographing of the photographic region CA based on the designation content fixed by the set button 341. The mode button 344 is manipulated to select various modes. The photography mode selection screen MSW in FIG. 10 is displayed by manipulating the mode button 344 to be selected. The mode button 344 is a button that switches among the pseudo intraoral radiography mode, the CT photography mode, the panoramic photography mode, and the cephalic photography mode. In other words, the mode button 344 acts as a photography mode switching part that switches the photography mode performed by the X-ray photography apparatus 1. The return button 345 is manipulated to return to the initial screen (for example, photography mode setting screen MSW indicated in FIG. 10).

In the photographic region setting screen 300, the photographic region of the CT photography can be set or the photographic region of the pseudo intraoral radiography can be set. The photographic region setting screen 300 can be also used in the panoramic photography. In other words, one of the upper jaw, the lower jaw, and the upper and lower jaws is selected through the upper and lower jaw selection portion 320 on the photographic region setting screen 300, and the panoramic photography may be performed to the selected site. It is considered that partial panoramic photography can be performed in the dental arch image 211 displayed on the image display portion 310. In the partial panoramic photography, the panoramic photography is performed only to the portion (that is, part of the dental arch) in which the photographic region CA is designated. The unnecessary X-ray exposure can be avoided by restricting the region on which the panoramic photography is performed.

In order to set the photographic region CA, the photographic region line 313 is set in the photographic region setting screen 300 displayed on the manipulation display part 61 so as to surround a photographing target object OB. Particularly, one of the upper jaw, the lower jaw, and the upper and lower jaws is selected in the upper and lower jaw selection portion 320 according to the position of the photographing target object. In the dental arch image 211 displayed in the image display portion 310, the center of the photographic region line 313 is designated through the designation cursor 312, and the radius (or a diameter) of the photographic region line 313 is input to a text box 331. The position and the size of the photographic region line 313 are set such that the local photographing target object is surrounded by the photographic region line 313.

In the case that the photographic region line 313 set in this manner is directly used as the photographic region CA, the photographic region CA is a solid cylinder having a true circle shape in a planar view. The height of the solid cylinder is determined according to the region (the upper jaw, the lower jaw, or the upper and lower jaws) designated through the upper and lower jaw selection portion 320. For the CT photography, the photographic region CA of the cylindrical body is irradiated with the X-ray cone beam BX1. For the pseudo intraoral radiography, the tooth included in the set photographic region CA is the photographing target. Accordingly, the manipulation display part 61 (or the manipulation display part 62) acts as a photographic region designation receiving part 610 (see FIG. 3) that designates the photographic region (the pseudo intraoral radiography region) of the pseudo intraoral radiography.

In the CT photography, when the extent of the photographic region CA viewed in the axial direction of the body axis MX1 of a patient is determined, the extent of the photographic region CA may be selected from one of at least "local (for example, the diameter of about 40 mm including part of the jaw)" and "wide (for example, the diameter of about 100 mm including the entire jaw)." In this case, the photography mode of the main body 2 is set to the local CT photography mode by setting "local" through the mode setter 601 of the main body controller 60, and the photography mode of the main body 2 is set to the wide CT photography mode by selecting "wide". The X-ray beam forming mechanism 13 may form the X-ray cone beam BX1 according to the size of the set CT photographic region to perform the local CT photography or the wide CT photography.

On the photography mode selection screen MSW, a selection screen for selecting one of the local CT photography mode and the wide CT photography mode may be displayed in the case that the CT photography mode button CM is manipulated to be selected. The local CT photography mode or the wide CT photography mode may be set based on the selection manipulation on the selection screen.

In the above explanation, the manipulation display part 61 (or the manipulation display part 62) includes the touch panel, and the setting manipulation of the photographic region CA is received by manipulating the designation cursor 312 displayed on the photographic region setting screen 300. Alternatively, the manipulation display part 61 may include the liquid crystal screen, and the setting manipulation of the photographic region CA may be received through a pointing device such as a mouse or a manipulation button placed near the manipulation display part 61.

In the above explanation, the photographic region setting screen 300 is displayed on the manipulation display part 61 to receive the setting manipulation of the photographic region CA. Alternatively, the photographic region setting screen 300 may be displayed on the display part 81 of the image processing device 8, and the setting manipulation of the photographic region CA may be received in the image processing device 8.

<Another Example of Photographic Region Setting Screen>

FIG. 12 is a view indicating another photographic region setting screen 300A. Like the photographic region setting screen 300 indicated in FIG. 11, the photographic region setting screen 300A includes an image display portion 310A, the upper and lower jaw selection portion 320, and the condition setting portion 340. In the photographic region setting screen 300A, the functions of the upper and lower jaw selection portion 320 and the condition setting portion 340 are similar to those of the upper and lower jaw selection portion 320 and the condition setting portion 340 in the photographic region setting screen 300. The photographic region setting screen 300A indicated in FIG. 12 has a feature point that a picture (a panoramic image 211A) of dental arch viewed in the Y-axis direction is displayed.

Instead of the dental arch image 211, the panoramic image 211A obtained by previously performing the panoramic photography to the dental arch region of the subject M1 using the X-ray is displayed in the image display portion 310A. In the image display portion 310A, the photographic region CA is set on the panoramic image 211A. In other words, the panoramic image 211A is used as the region designating image. In the example indicated in FIG. 12, a photographic region line 313A is set first. Although not illustrated, the photographic region line 313A is designated using the designation cursor 312. In FIG. 12, the size of the photographic region line 313A may arbitrarily be changed as indicated by the solid line and the alternate long and two-short dashed line.

In the image display portion 310A, designation information that is input to designate the photographic region CA with respect to the panoramic image 211A is transmitted to the image processing device 8. The image processing device 8 transmits the information on the photographic region line 313A corresponding to the received designation information to the manipulation display part 61.

The manipulation display part 61 that receives the information on the photographic region line 313A displays the panoramic image 211A and the photographic region line 313A based on the received information in the image display portion 310A of the photographic region setting screen 300A while superimposing the panoramic image 211A and the photographic region line 313A on each other. After the superposition display, a processing flow is similar to that of the photographic region setting screen 300.

Three-dimensional positional information on a panoramic cross-sectional position of the subject M1 fixed to the subject retention part 421 can be easily identified by calculation processing of the image processor 801b from the positional relationship between the subject retention part 421 and the panoramic cross-sectional position being set. Accordingly, three-dimensional coordinates at a position designated with respect to the panoramic image 211A is acquired by the calculation.

The panoramic image 211A is not limited to the panoramic image acquired by the X-ray photography apparatus 1, but the panoramic image acquired by another photographing apparatus may be used. In this case, if the positional information on the panoramic cross-section at the time of the panoramic photography is known, the three-dimensional coordinates at the position designated on the panoramic image 211A can be acquired by the calculation.

Figure 13:
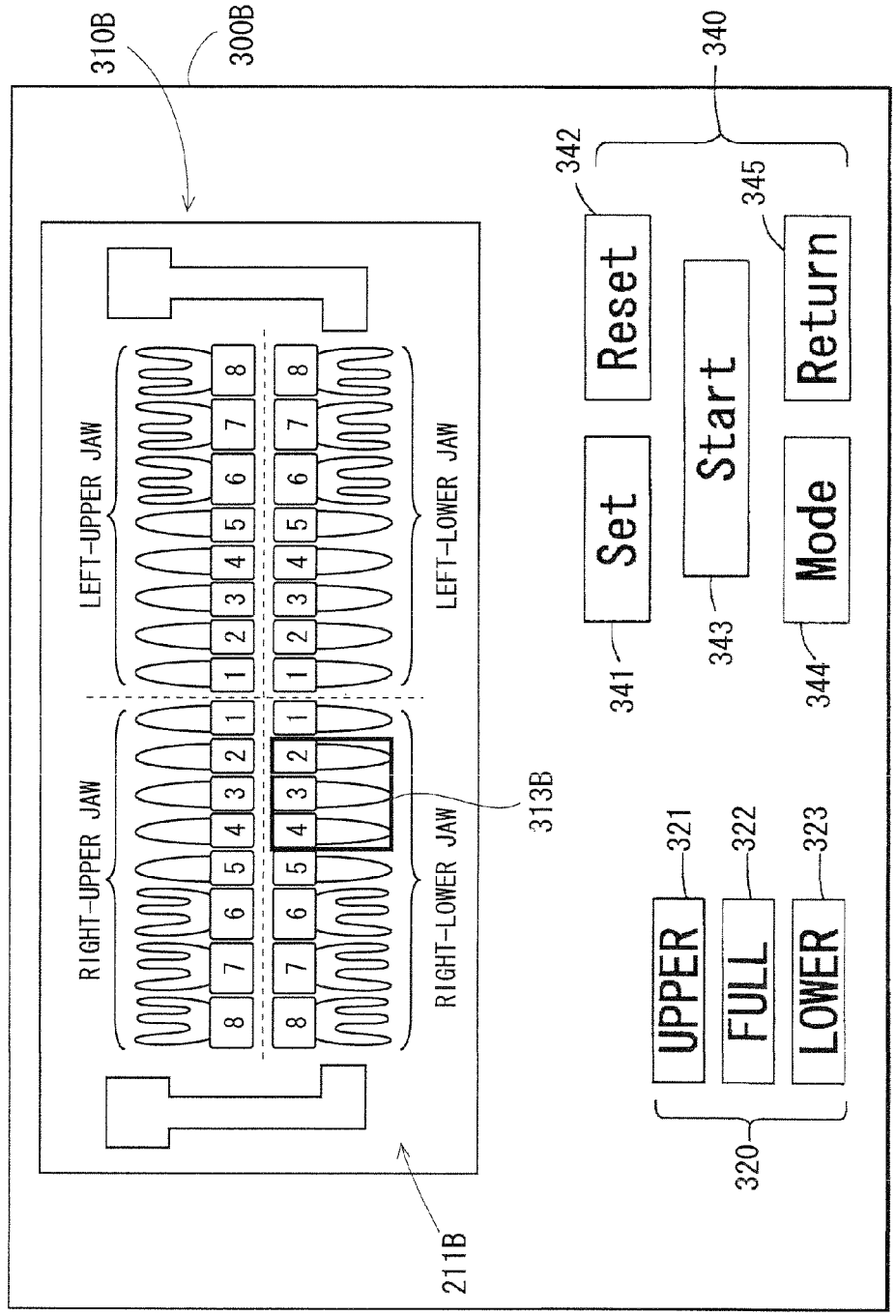

FIG. 13 is a view indicating another photographic region setting screen 300B. In the photographic region setting screen 300A in FIG. 12, the photographed image obtained by performing the panoramic photography to the subject M1 is displayed as the panoramic image 211A in the image display portion 310A. However, it is not always necessary that the panoramic image 211A be the photographed image. In the photographic region setting screen 300B in FIG. 13, an illustration 211B which is an imitation of the photographed panoramic image is displayed in an image display portion 310B. Illustrations of the eight teeth are drawn in the illustration 211B in each of the right-upper jaw, the left-upper jaw, the right-lower jaw, and the left-lower jaw. The rectangular photographic region line 313B is set on the illustration 211B. It is not always necessary that the panoramic image 211A be obtained by performing the panoramic photography to the subject M1. For example, the panoramic cross-section image of the jaw of a standard skeleton or the illustration which is an imitation of the photographed panoramic image may be used as the panoramic image 211A.

In the above explanation, the photographic region setting screen 300 is displayed on the manipulation display part 61 to receive the setting manipulation of the photographic region CA. Alternatively, the photographic region setting screen 300 may be displayed on the display part 81 of the image processing device 8, and the setting manipulation of the photographic region CA may be received in the image processing device 8.

The collected frame data is sequentially transferred to the image processing device 8, and stored in a storage part 802. The image processor 801b performs the calculation processing to the collected frame data according to each photography mode. For example, for the CT photography, the frame data is reconstructed into three-dimensional data.

The pseudo intraoral radiography mode can be configured such that photographic region CA is set to the upper jaw by the UPPER button 321, or such that the photographic region CA is set to the lower jaw by the LOWER button 323.

For the pseudo intraoral radiography mode, the photographic region line 313 may be used in setting the photographic region CA. Alternatively, as indicated in FIG. 11, an oval photographic region line 314 may be displayed along the dental arch, and the photographic region CA corresponding to the oval photographic region line 314 may be set.

For the pseudo intraoral radiography mode, because a specific tooth is the photographing target unlike in the CT photography mode, it is not necessary that the region irradiated with the X-ray be strictly displayed as the photographic region. Accordingly, the photographic region may be set by not the photographic region lines 313 and 314 indicating a closed region but by a simple line 315 indicating the cross-section. The photographic region lines 313 and 314 and the line 315 may simultaneously be displayed.

The region fixed in each tooth may be set to the photographic region CA indicated by the photographic region lines 313 and 314 or the line 315, or the size and the position of the photographic region CA may variably be adjusted. For example, the variable adjustment can be performed by moving the photographic region lines 313 and 314 or the line 315 through manipulation to move a pointer based on mouse manipulation. According to the adjusted region, the X-ray beam forming mechanism 13 adjusts the width of the X-ray cone beam BX1, or the moving mechanism 200 adjusts the position of the turning arm 30.

For the panoramic photography, the photographing target such as the panoramic photography of the entire jaw, the panoramic photography of only the upper jaw, and the panoramic photography of only the lower jaw may be selected by adjusting the positions of the vertically-shielding plates 14 and the horizontally-shielding plates 15. In this case, it is considered that the photographic region CA is set to the upper jaw by the UPPER button 321, set to the lower jaw by the LOWER button 323, and set to the upper and lower jaws, namely, the entire jaw by the FULL button 322.

Additionally, the setting can be performed such that partial panoramic photography in which only the panoramic photography is performed to the partial region of the dental arch, and the photographic region line may be set on the photographic region setting screen 300 in the designated range of the partial region like the pseudo intraoral radiography. At this point, the manipulation can be performed like the designation of the photographic region in the pseudo intraoral radiography mode.

<Irradiation Direction of X-Ray Beam>
<<Control of Irradiation Direction During Panoramic Photography>>

Figure 14:
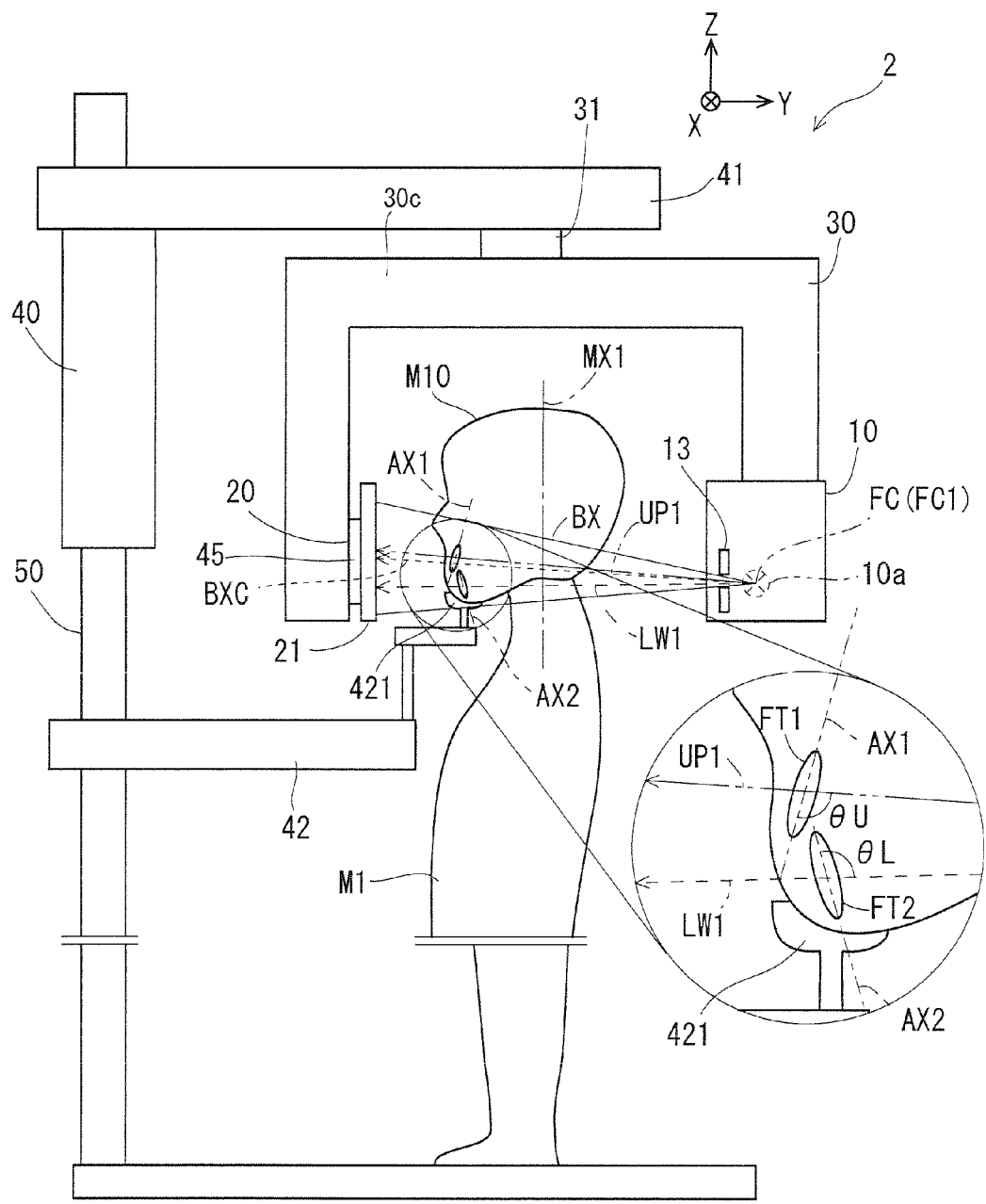
FIG. 14 is a view indicating an irradiation direction of an X-ray beam during panoramic photography.

FIG. 14 is a view illustrating the irradiation direction of the X-ray beam BX during the panoramic photography. FIG. 14 illustrates a state in which the subject M1 is irradiated from straight behind with the X-ray beam BX (specifically, the X-ray slit beam). As indicated in FIG. 14, in the panoramic photography, since it is sufficient that the upper and lower portions of the X-ray beam BX include the upper and lower jaws in the head M10 of the subject M1, there is no particular limitation to the irradiation direction of the X-ray beam BX. For example, an angle $\theta U$ formed by an X-ray UP1 transmitted through the center portion of an upper jaw anterior tooth FT1 and a tooth axis AX1 of the upper jaw anterior tooth FT1 is not 90 degrees, and an angle $\theta L$ formed by an X-ray LW1 transmitted through the center portion of a lower jaw anterior tooth FT2 and a tooth axis AX2 of the lower jaw anterior tooth FT2 is not 90 degrees. However, the irradiation direction during the panoramic photography is controlled such that a center axis BXC of the X-ray beam BX is oriented upward with respect to the direction (in this case, the horizontal direction such as the Y-axis direction) orthogonal to the axial direction of a body axis MX1. In the X-ray photography apparatus 1, the elevating part 40 and the X-ray beam forming mechanism 13 can relatively change the irradiation direction of the X-ray beam BX to the head M10 of the subject M1 with respect to the axial direction of the body axis MX1. The X-ray beam forming mechanism 13 is an example of the irradiation direction changing part.

<<Control of Irradiation Direction During Pseudo Intraoral Radiography>>

Figure 15:
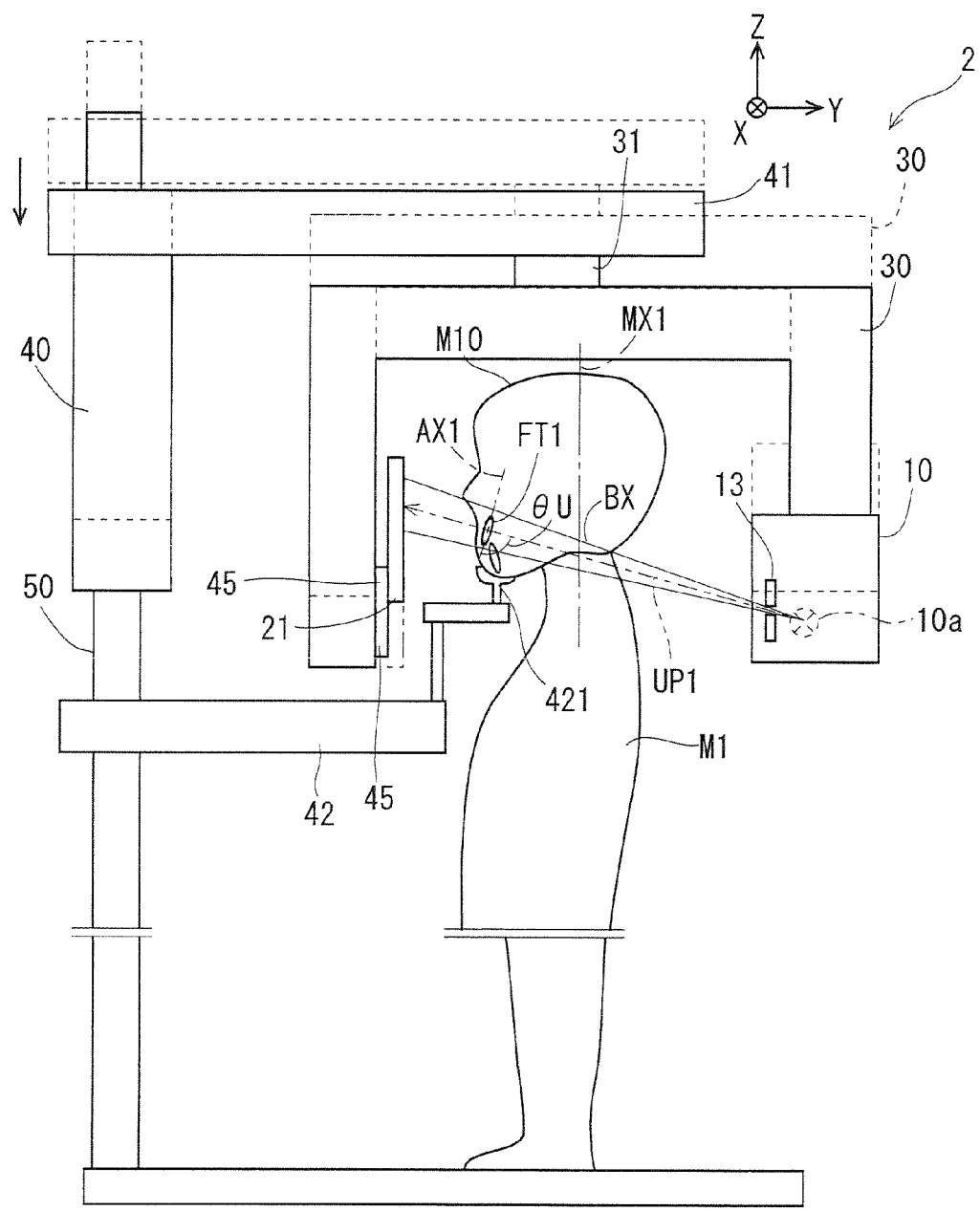
FIG. 15 is a view indicating an irradiation direction of the X-ray beam during pseudo intraoral radiography in which an upper jaw anterior tooth is set to a photographing target.

FIG. 15 is a view illustrating the irradiation direction of the X-ray beam BX during the pseudo intraoral radiography in which the upper jaw anterior tooth FT1 is set to the photographing target. As indicated in FIG. 15, in the pseudo intraoral radiography, the upper jaw anterior tooth FT1 is irradiated with the X-ray beam BX such that an X-ray UP1 passing through the center portion of the upper jaw anterior tooth FT1 is orthogonal to the tooth axis AX1 of the upper jaw anterior tooth FT1 that is part of the row of teeth (that is, the angle $\theta U$ is 90 degrees). At this point, the upper portion of the tooth axis AX1 of the upper jaw anterior tooth FT1 is inclined toward the rear side (that is, the +Y-side) of the subject M1, and the lower portion of the tooth axis AX1 is inclined toward the front side (that is, the −Y-side) of the subject M1. Therefore, it is necessary to upwardly control the irradiation direction of the X-ray beam BX. The X-ray UP1 may not be strictly orthogonal to the tooth axis AX1, but the X-ray UP1 may substantially be orthogonal to the tooth axis AX1.

In the X-ray tube of the X-ray generator 10a, a thermal electron generated by a negative electrode collides with a positive electrode, thereby generating the X-ray. The X-ray travels while spreading with a point at which the thermal electron collides with the positive electrode as a starting point. Occasionally, the starting point at which the X-ray is generated is referred to as an actual focal spot, and the actual focal spot viewed in the direction in which the upper jaw anterior tooth FT1 is irradiated with the X-ray is referred to as an effective focal spot. In FIG. 14, the actual focal spot and the effective focal spot are designated by an actual focal spot FC and an effective focal spotFC1. The X-ray UP1 is generated from the effective focal spotFC1, and passes through the center portion of the upper jaw anterior tooth FT1.

In the example indicated in FIG. 15, in order to perform the irradiation with the X-ray beam BX, the turning arm 30 (the support) is lowered below the height (indicated by a broken line) in the panoramic photography by driving the elevating part 40. The position of the X-ray generator 10a (more particularly, the position of the effective focal spot FC1) is lowered with respect to the head of the subject M1 (the test subject) by lowering the turning arm 30, which allows the irradiation direction of the X-ray beam BX to be oriented upward. In other words, the elevating part 40 acts as a third elevating mechanism that vertically displaces the turning arm 30 in parallel with the axial direction of the turning shaft 31 to change the height position at which the X-ray beam BX is emitted. Because the turning arm 30 is elevated and lowered with respect to the subject M1, the subject M1 does not need to be elevated and lowered. Therefore, the burden placed on the subject M1 (the test subject) can be reduced.

The photographing in FIG. 15 is controlled such that the irradiation direction (the axial direction of the center axis BXC of the X-ray beam BX) of the X-ray beam BX is oriented upward by driving the X-ray beam forming mechanism 13. The X-ray beam forming mechanism 13 relatively changes the irradiation direction of the X-ray beam BX to the head M10 of the subject M1 with respect to the axial direction of the body axis MX1. In other words, the beam forming mechanism 13 vertically changes the irradiation direction of the X-ray beam BX along the axial direction of the body axis MX1. As described above, the irradiation direction of the X-ray beam BX is changed by the shielding-plate vertically-moving mechanism 16a (see FIG. 4) serving as the first elevating mechanism of the X-ray beam forming mechanism 13. In conjunction with the change of the irradiation direction by the first elevating mechanism, an X-ray-detector drive part 45 that acts as a second elevating mechanism is driven to elevate the X-ray detector 21 to a predetermined height such that the X-ray beam BX is incident to the detection surface without trouble. The X-ray-detector drive part 45 is controlled by an X-ray-detector drive controller 603 (see FIG. 3) of the main body controller 60.

Although not illustrated, for example, the X-ray-detector drive part 45 is constructed by a member that guides the X-ray detector 21 along the Z-direction and a roller that is fixed to the shaft of a motor fixed in the base portion of the X-ray-detector drive part 45, and the X-ray detector 21 is driven to be elevated and lowered while the roller abuts on the rear surface of the X-ray detector 21. Alternatively, the X-ray-detector drive part 45 is constructed by a member that guides the X-ray detector 21 along the Z-direction and a male screw portion in which a female screw portion fixed to the rear surface of the X-ray detector 21 is turnably fixed to the base portion of the X-ray-detector drive part 45, and the X-ray detector 21 is elevated and lowered in the Z-direction by the motor as which is the drive source.

In the dental arch having the general shape, since the upper portion of the upper jaw anterior tooth FT1 is on the rear side (that is, the +Y-side) of the subject M1, and the lower portion of the upper jaw anterior tooth FT1 is on the front side (that is, the −Y-side) of the subject M1 the tooth axis AX1 is inclined. On the other hand, the tooth axis of a tooth except the anterior tooth or a tooth near the anterior tooth is hardly inclined with respect to the direction toward the cheek side from the tongue side or an opposite direction thereto. Therefore, the irradiation direction of the X-ray beam BX for tooth except the anterior tooth or a tooth near the anterior tooth is set to the horizontal direction with respect to the axial direction of the body axis MX1 unlike the case that the pseudo intraoral radiography is performed to the anterior tooth. In other words, the irradiation direction of the X-ray beam BX varies with respect to the axial direction of the body axis MX1 according to the position of the pseudo intraoral radiography region.

<Correction of Distortion>

In the case that the pseudo intraoral radiography of the upper jaw anterior tooth FT1 is performed by the configuration in FIG. 15, the upper portion (the portion of tooth root side) is distant from the detection surface of the X-ray detector 21 while the lower portion (the portion of tooth crown side) is close to the detection surface of the X-ray detector 21. Therefore, a distortion is generated due to the difference in magnification rate in the X-ray image of the upper jaw anterior tooth FT1 obtained by the X-ray detector 21. Accordingly, the distortion is preferably corrected through the image processing. Specifically, the following processing is performed.

For convenience of explanation, it is assumed that FT1I (not illustrated) is the X-ray image of the upper jaw anterior tooth FT1 received by the detection surface of the X-ray detector 21, that EL1 is the magnification rate on the portion of tooth root side, and that EL2 is the magnification rate on the portion of tooth crown side. The magnification rate EL1 and the magnification rate EL2 in the X-ray image FT1I have a relationship of EL1>EL2. The ratio (vertical width/horizontal width) AS1 of the width in the vertical direction (the z-direction) of the X-ray image FT1I and the width of the horizontal direction (the x-direction) and The ratio (vertical width/horizontal width) AS2 of the real scale vertical width of the anterior tooth FT1 and the real scale horizontal width have a relationship of AS1>AS2.

One of the following pieces of image correction processing is performed.

Processing 1: the correction is performed such that EL1 becomes equal to EL2.

Processing 2: the correction is performed such that AS1 becomes equal to AS2.

Processing 3: the correction is performed such that EL1 becomes equal to EL2 and AS1 becomes equal to AS2.

Because the distortion also exists in a portion except the portion of tooth crown and the portion of tooth root, the magnification rate is corrected from the portion of tooth root to the portion of tooth crown. Therefore, the X-ray image FT1I can be brought similar to the X-ray image that is received by the X-ray detection surface disposed perpendicular to the X-ray UP1.

Preferably the correction is also performed, when the X-ray image received by the detection surface of the X-ray detector 21 has the distortion with respect to the real tooth while a tooth except the upper jaw anterior tooth FT1 is set to the photographing target.

Figure 16:
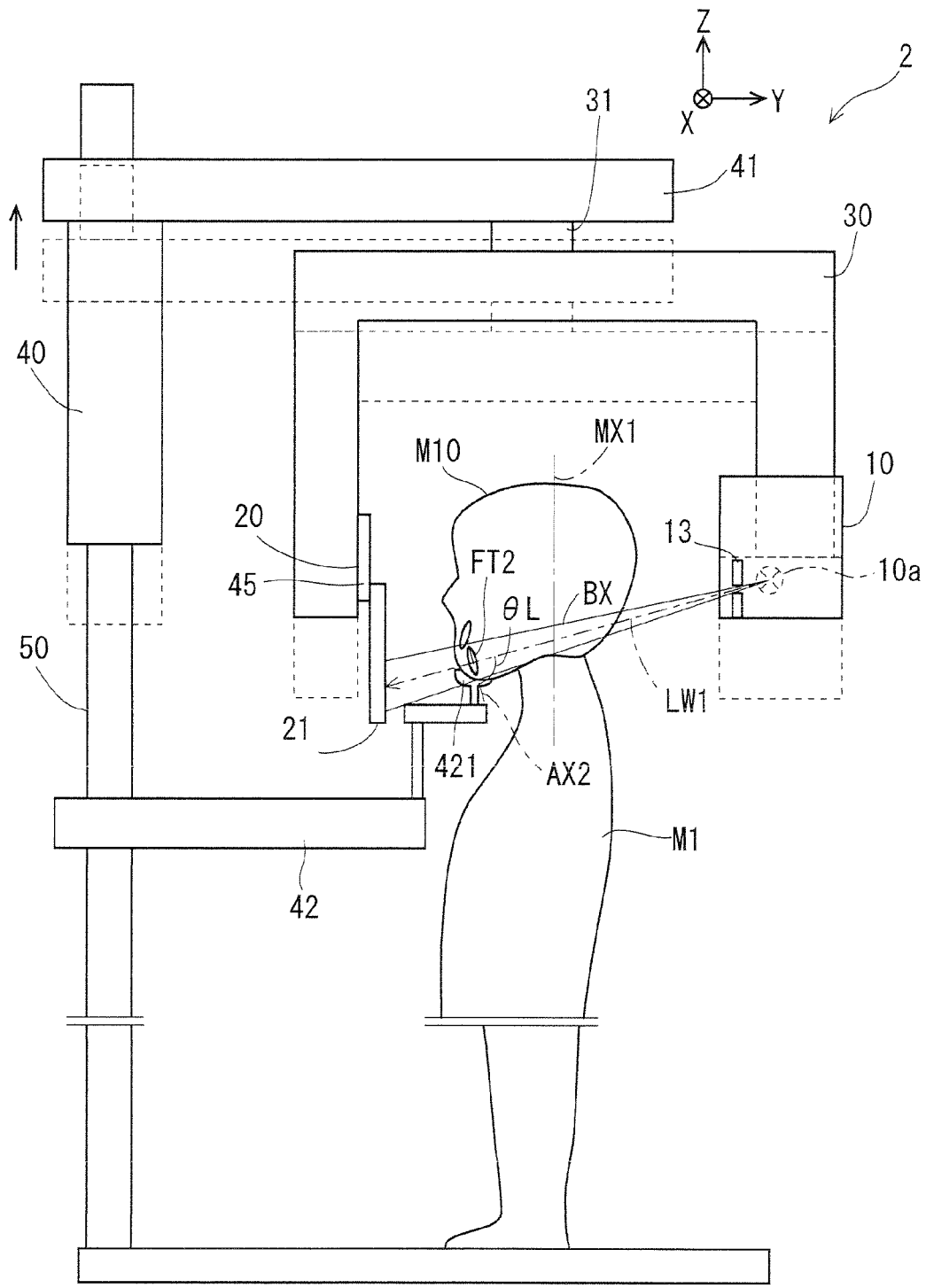
FIG. 16 is a view indicating an irradiation direction of the X-ray beam during the pseudo intraoral radiography in which a lower jaw anterior tooth is set to the photographing target.

FIG. 16 is a view indicating the irradiation direction of the X-ray beam BX during the pseudo intraoral radiography in which the lower jaw anterior tooth FT2 is set to the photographing target. In the tooth axis of the lower jaw anterior tooth FT2, the upper portion is inclined toward the front side (that is, the −Y-side) of the subject M1, and the lower portion is inclined onto the rear side (that is, +Y-side) of the subject M1. Therefore, it is necessary to downwardly control the irradiation direction of the X-ray beam BX.

In FIG. 16, in order to perform the irradiation with the X-ray beam BX, the turning arm 30 is elevated above the height (indicated by the broken line) in the panoramic photography by driving the elevating part 40. The irradiation direction of the X-ray beam BX is controlled by driving the X-ray beam forming mechanism 13 so as to be oriented downward. The X-ray detector 21 is lowered to the predetermined height by driving the X-ray-detector drive part 45 such that the X-ray beam BX is incident to the detection surface.

Basically, when the tooth is observed from the tongue side (the inside of the mouth cavity) toward the cheek side, or when the tooth is observed in the opposite direction, a sight line direction is desirably orthogonal to the tooth axis. The X-ray image in which the tooth is obliquely looked down from above or obliquely looked up from below is obtained, unless the center axis of the X-ray beam BX is orthogonal to the tooth of the photographing target. In this case, the image in which the tooth is looked shorter than the real size is obtained. Accordingly, the center axis of the X-ray beam is orthogonally incident to the target tooth (that is, the center axis of the X-ray beam BX is orthogonal to the tooth axis), which allows the acquisition of the image that is true to the shape of the tooth with little or no distortion. However, the center axis of the X-ray beam may not be strictly orthogonal to the target tooth, but it is sufficient that the center axis of the X-ray beam is substantially orthogonal to the target tooth.

The case that the lower jaw is set to the photographing target is similar to the case that the upper jaw is set to the photographing target in that the irradiation direction of the X-ray beam BX is varied with respect to the axial direction of the body axis MX1 depending on the position of the pseudo intraoral radiography region. More specifically, the irradiation angle of the X-ray beam BX with respect to the Z-axis direction, the irradiation range, the position of the turning arm 30, and the turning angle of the turning arm 30 vary in each of the photographic regions of the photographing targets such as the entire jaw, part of the jaw, the tooth of the upper jaw, the tooth of the lower jaw, the tooth in a certain region of the upper jaw, and the tooth in a certain region of the lower jaw. Therefore, in each photographic region, the elevating control of the elevating part 40 is performed by the support drive controller 602, the position control of the turning arm 30 is performed by the moving mechanism 200, the drive control of the X-ray beam forming mechanism 13 is performed by the X-ray-regulating-part drive part 101 based on the control of the X-ray-regulating-part drive controller 605, and the position control of the X-ray detector 21 is performed by the X-ray-detector drive part 45 based on the control of the X-ray-detector drive controller 603, as necessary. In the case that the subject-retention-part drive part MH1 needs to drive the subject retention part 421, the subject-retention-part drive part MH1 is properly controlled based on the control of a subject-retention-part drive controller 604.

<<Control of Irradiation Direction During CT Photography>>

Figure 17:
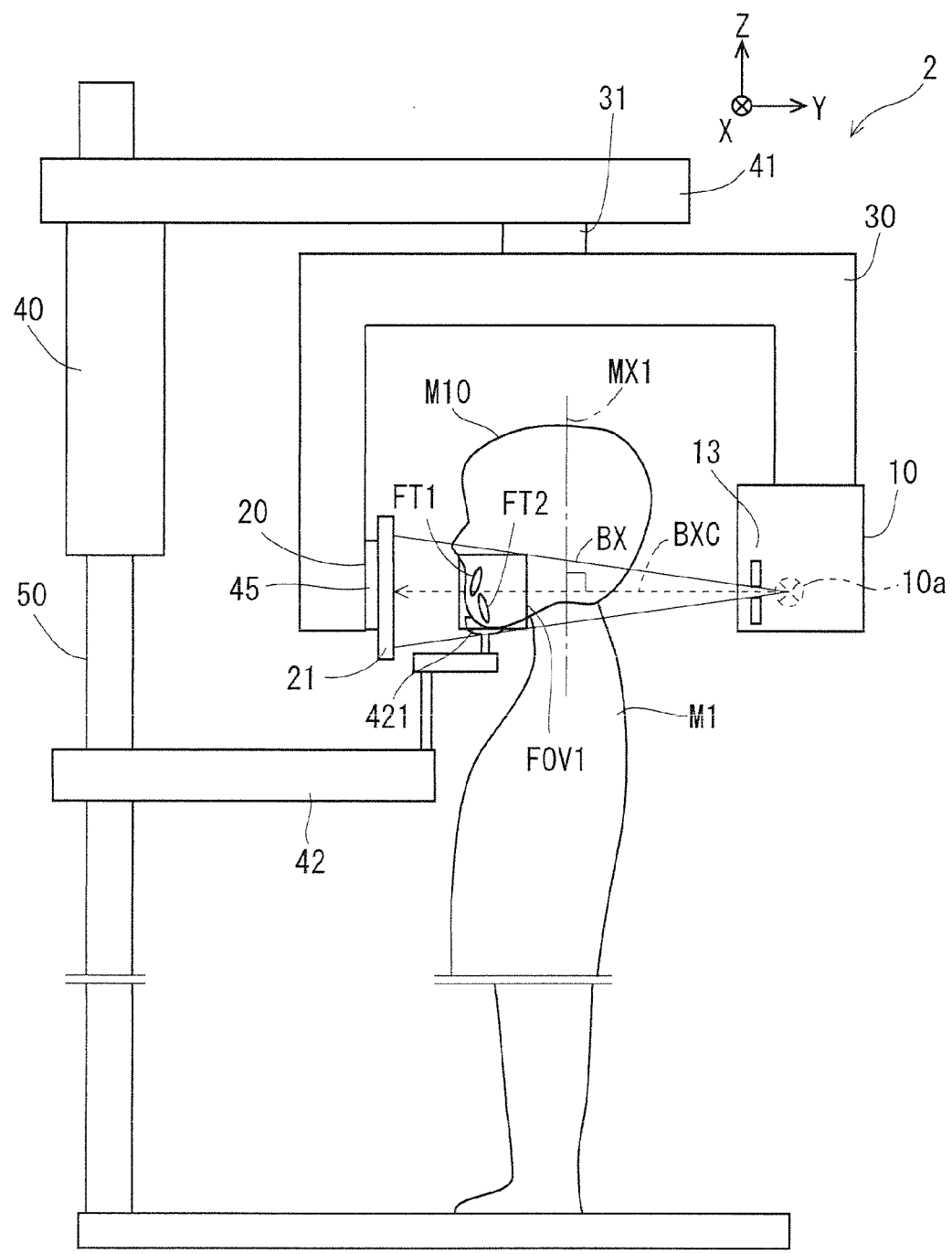
FIG. 17 is a view illustrating an irradiation direction of the X-ray beam during CT photography in which the upper jaw and the lower jaw are set to the photographing target.

FIG. 17 is a view indicating the irradiation direction of the X-ray beam BX during CT photography in which the upper jaw and the lower jaw are set to the photographing target. In the CT photography, the photographic region (Field of View (FOV)) is irradiated with the X-ray beam BX in multiple directions included in the angle range of at least 180 degrees. At this point, the irradiation direction of the X-ray beam is controlled such that the center axis BXC of the X-ray beam passes through the center portion of the photographic region. For example, in the CT photography in FIG. 17, a solid-cylinder photographic region FOV1 is irradiated with the X-ray beam BX. The photographic region FOV1 has a diameter of about 80 mm to about 100 mm, and includes both the upper jaw and the lower jaw. The photographic region FOV1 extends along the body axis MX1. In the case that the photographic region FOV1 is set to the photographing target, as indicated in FIG. 17, the photographic region FOV1 is irradiated with the X-ray beam BX such that the center axis BXC of the X-ray beam BX is transmitted through the center of the photographic region FOV1, and such that the center axis BXC is orthogonal to the body axis MX1. Because the body axis MX1 is parallel to the Z-axis direction, the center axis BXC is parallel to an XY plane (a horizontal plane).

Although not illustrated, in the X-ray photography apparatus 1, the CT photography can be performed while some teeth of the upper jaw (or the lower jaw) or the gum is set to the photographing target. In this case, the CT photography is performed while the photographic region is made narrower than the photographic region FOV1 in FIG. 17. Even in this case, the irradiation direction of the X-ray is controlled such that the center axis BXC of the X-ray beam BX is transmitted through the center of the relatively small photographic region, and such that the center axis BXC is orthogonal to the body axis MX1.

<Pseudo Intraoral Radiography>

Figure 18:
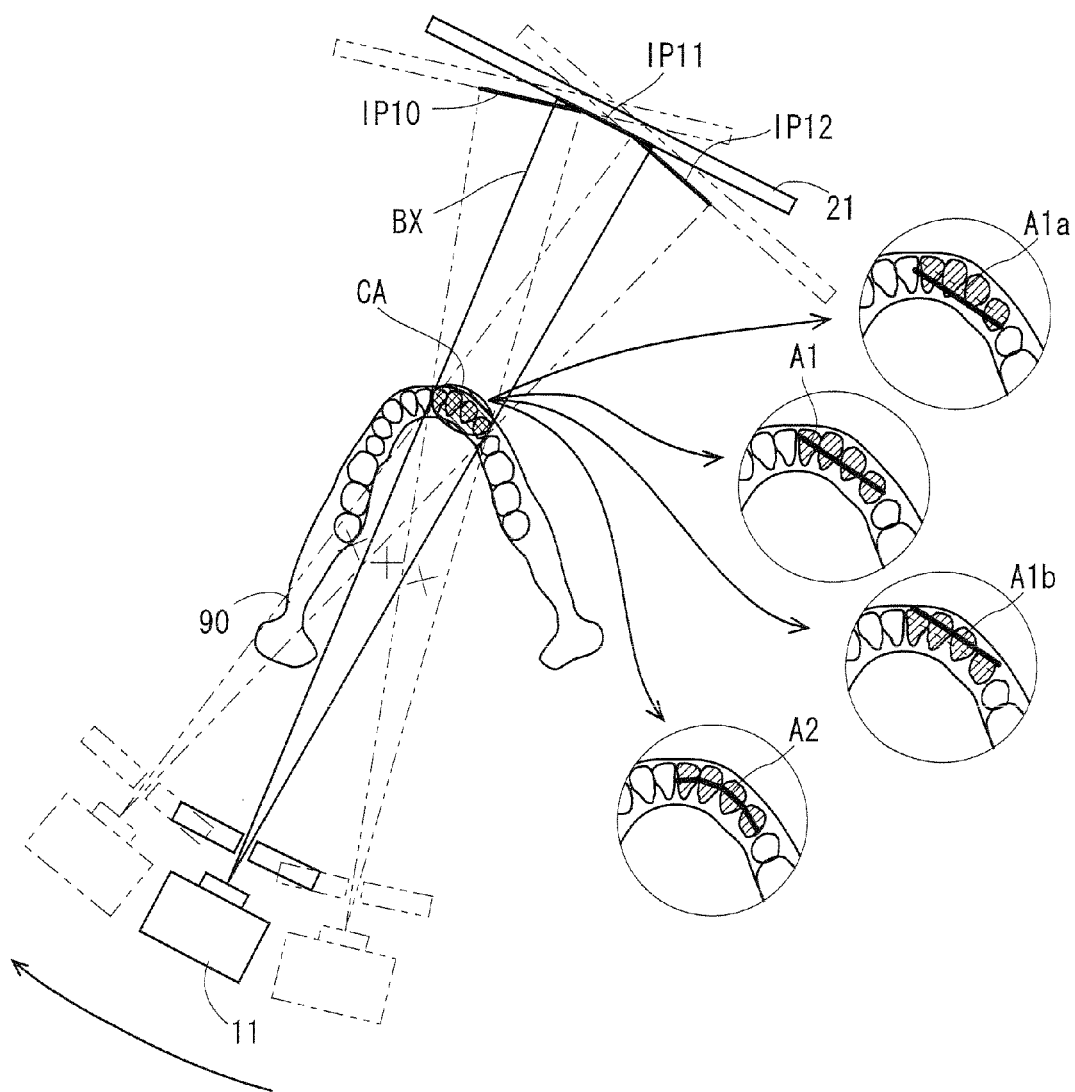
FIG. 18 is a schematic plan view illustrating a situation of the pseudo intraoral radiography when viewed toward a −Z-direction from a +Z-side.

FIG. 18 is a schematic plan view indicating a situation of the pseudo intraoral radiography when viewed toward the −Z-direction from the +Z-side. In FIG. 18, four teeth on the right side in the lower jaw are set to the photographing target. The teeth serving as the photographing target are designated through the photographic region setting screen 300 indicated in FIG. 11.

As indicated in FIG. 18, in the pseudo intraoral radiography, like the conventional tomosynthesis, the X-ray generator 10a and the X-ray detector 21 are turned by angles of 180 degrees or less (for example, about 15 degrees to about 50 degrees) while the head M10 of the subject M1 is interposed therebetween, whereby the photographing target object (in this case the four teeth) is irradiated with the X-ray beam BX in multiple directions. The tomographic image of any cutting plane (tomographic plane) is reconstructed by the method of stacking (the shift-and-add method), in which the projection images obtained by performing the photographing from the plural directions are overlapped while shifted by a proper amount in accordance with the turning direction, and the filtered back projection in which a filter is used. The image processing is described later in detail.

During the X-ray photography, the movement control of the turning arm 30 is implemented by controlling the turning center of the X-ray generator 10a and the X-ray detector 21 to be set to a place different from the turning shaft 31 using the XY table. Alternatively, the movement control of the turning arm 30 may be performed such that the center of the turning shaft 31 is located in the center or the neighborhood of the center of the photographing target region using the XY table, and the X-ray photography may be performed while the turning shaft 31 is not moved but the turning arm 30 is turned.

In the pseudo intraoral radiography, even if a spread of the X-ray beam BX is made narrower than the photographic region CA (the pseudo intraoral radiography region), the tomographic image in the photographic region CA can tentatively be generated by increasing the turning angle of the turning arm 30. However, when the spread of the X-ray beam BX is wider than at least the photographic region CA, the X-ray projection image data having wealth of information on X-ray absorption in the photographic region CA can be collected even at the small turning angle. Therefore, the tomographic image can be generated without trouble.

In reconstructing the tomographic image, the position of the cutting plane may arbitrarily be set with respect to the direction (in this case, the horizontal direction) perpendicular to the axial direction of the turning shaft 31. For example, as indicated in FIG. 18, the position of the cutting plane can be set to a planar cutting plane A1 passing through the substantial center of the photographic region CA, a planar cutting plane A1a located outside the head M10 with respect to the planar cutting plane A1, or a planar cutting plane A1b located inside the head M10 with respect to the planar cutting plane A1. Therefore, the tomographic image, which focuses on the position that the reader wants to observe, can be generated.

As indicated in FIG. 18, the position of the cutting plane can be set to the planar cutting plane A1, and also set to a curved cutting plane A2 in accordance with a dental arch 90. The dental arch 90 may have a standard shape or a shape identified by an actual teeth mark of the subject M1 or the X-ray photograph.

The position and shape of the cutting plane can be arbitrarily determined by a reconstruction calculation method, namely, by properly changing the shift amount during the stacking. Accordingly, the position and shape of the cutting plane may arbitrarily be set according to the purpose of the image diagnosis.

The panoramic photography is performed to make the diagnosis of the relatively wide range such as the entire upper jaw, the entire lower jaw, and the entire upper and lower jaws. On the other hand, the pseudo intraoral radiography is performed to make the diagnosis of the local portion such as part of the row of teeth or the gum. Therefore, in the pseudo intraoral radiography, desirably the photographing target object can be observed while magnified as large as possible. In the preferred embodiment, the main body controller 60 controls a moving part 202 to change the distance between the X-ray detector 21 and the head M10, whereby the magnification rate of the obtained X-ray projection image is changed between the pseudo intraoral radiography and the panoramic photography.

More specifically, in the pseudo intraoral radiography, the distance between the X-ray detector 21 and the head M10 is maintained so as to be longer than that of the panoramic photography. Therefore, in the pseudo intraoral radiography, the magnification rate of the identical site can be increased compared with the panoramic photography. Accordingly, the photographing target object can be largely photographed, and the tomographic image suitable for the diagnosis can be obtained.

Spatial resolution of the X-ray detection of the X-ray detector 21 may be changed according to the CT photography or the pseudo intraoral radiography. Therefore, the X-ray projection image having the spatial resolution suitable for each of the pseudo intraoral radiography and the CT photography can be acquired. For example, the fine projection data can be obtained in high resolution during the CT photography, and the CT image (the tomographic image) having the excellent resolution can be generated. Similarly, the spatial resolution of the X-ray detection of the X-ray detector 21 may be changed according to the panoramic photography and the pseudo intraoral radiography. Therefore, the X-ray projection image having the spatial resolution suitable for each of the pseudo intraoral radiography and the panoramic photography can be acquired.

<Method of Stacking (Shift-and-Add Method)>

Figure 19:
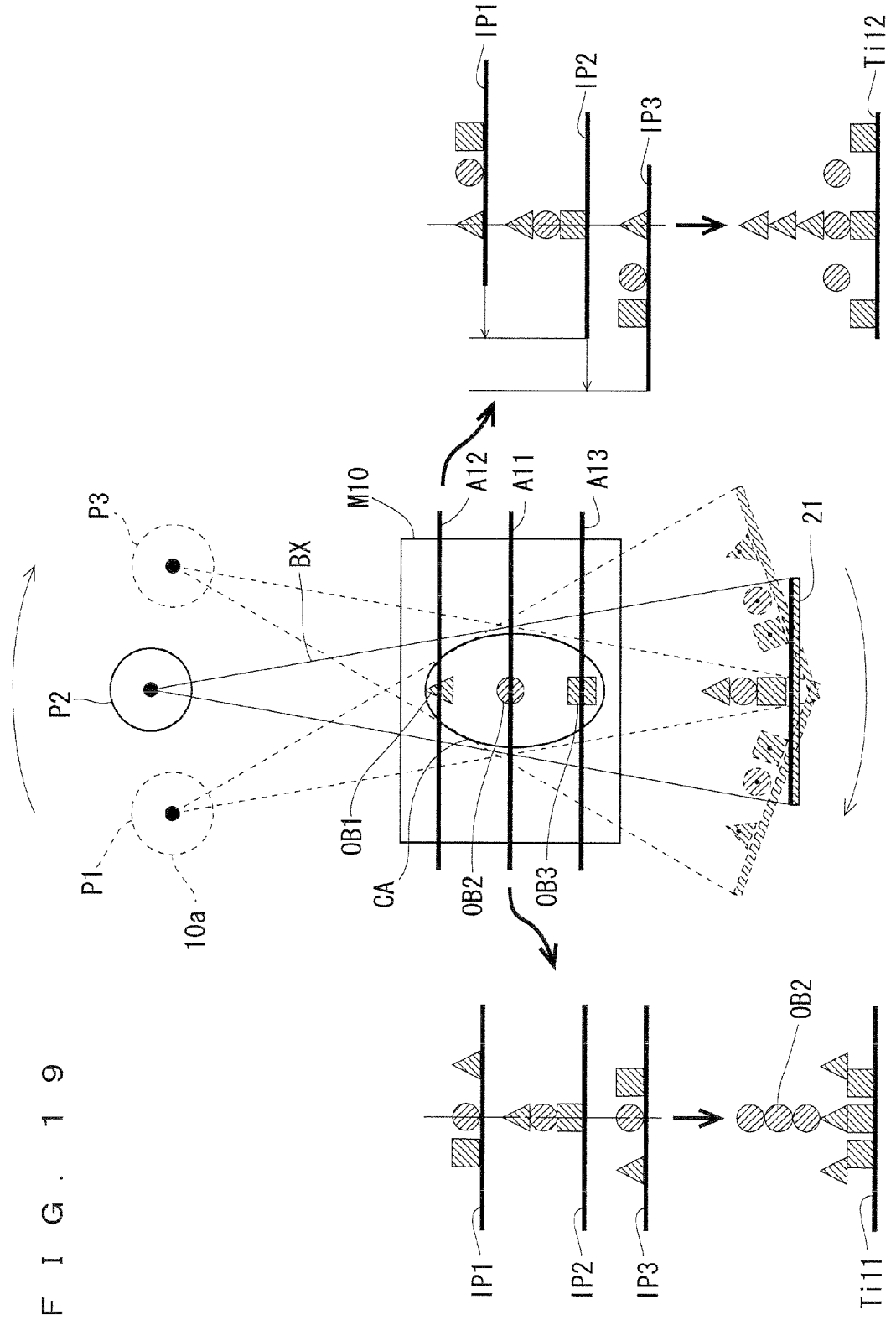
FIG. 19 is an explanatory view illustrating a process in which a tomographic image is acquired by applying a method of stacking to frame data acquired by the pseudo intraoral radiography.

FIG. 19 is an explanatory view indicating a process in which the tomographic image is acquired by applying the method of stacking to the frame data acquired by the pseudo intraoral radiography. Referring to FIG. 19, in the head M10 of the subject M1, it is assumed that an object OB1 (indicated by a triangle), an object OB2 (indicated by a circle), and an object OB3 (indicated by a quadrangle) are arrayed in this order in line in the direction toward the side of the X-ray detector 21 from the side of the X-ray generator 11*a*. In the pseudo intraoral radiography, the movement of the turning arm 30 is controlled such that the X-ray beam BX (the X-ray cone beam) turns about the object OB2. It is assumed that the X-ray generator 10*a* moves to a position P3 from a position P1 via a position P2. The X-ray projection images expressed by the pieces of frame data acquired in the positions P1 to P3 are referred to as X-ray projection images IP1, IP2, and IP3.

When the X-ray generator 10*a* is located at the position P2, the irradiation direction (the axial direction of the center axis BXC) of the X-ray beam BX is parallel to the direction in which the objects OB1 to OB3 are arrayed. For this reason, all the objects OB1 to OB3 are photographed in the center portion of the X-ray projection image IP2. On the other hand, when the X-ray generator 10*a* is located at the positions P1 and P3, although the object OB2 is photographed in the center portions of the X-ray projection images IP2 and IP3, the objects OB1 and OB3 are photographed while shifted rightward or leftward from the center.

In the case that the cutting plane used to reconstruct the tomographic image is set to a planar cutting plane A11 passing through the object OB2, a tomographic image Ti11 is acquired by simply superposing the acquired X-ray projection images IP1, IP2, and IP3 (that is, by superposing the X-ray projection images IP1, IP2, and IP3 without shifting the X-ray projection images IP1, IP2, and IP3) as indicated on the left side in FIG. 19. In the tomographic image Ti11, the information content related to the objects OB1 and OB3 are dispersed right and left, and the information content related to the three objects OB2 concentrate on the center portion. Therefore, the tomographic image Ti11 having the much information on the X-ray absorption of the object (for example, the object OB2) located on the planar cutting plane A11 can be obtained. In other words, the tomographic image Ti11 in which the object located on the planar cutting plane A11 is largely weighted can be acquired.

On the other hand, in the case that the cutting plane is set to a planar cutting plane A12 passing through the object OB1, the X-ray projection images IP1 to IP3 are stacked while shifted by required amounts in required directions, thereby acquiring a tomographic image Ti12 as indicated on the right side in FIG. 19. Specifically, because the object OB1 is located in the center portion of the planar cutting plane A12, the X-ray projection images IP1 to IP3 are shifted to the right or left side such that the object OB1 is photographed in the center, whereby the pieces of information on the three objects OB1 are collected in the center portion. Therefore, the tomographic image Ti12 having much information on the X-ray absorption of the object (for example, the object OB1) located on the planar cutting plane A12 can be obtained.

Although not illustrated, in the case that the cutting plane is set to a planar cutting plane A13 passing through the object OB3, similarly, the X-ray projection images IP1 to IP3 are stacked while shifted by required amounts in required directions, which allows the tomographic image related to the cutting plane to be obtained.

Figure 20:
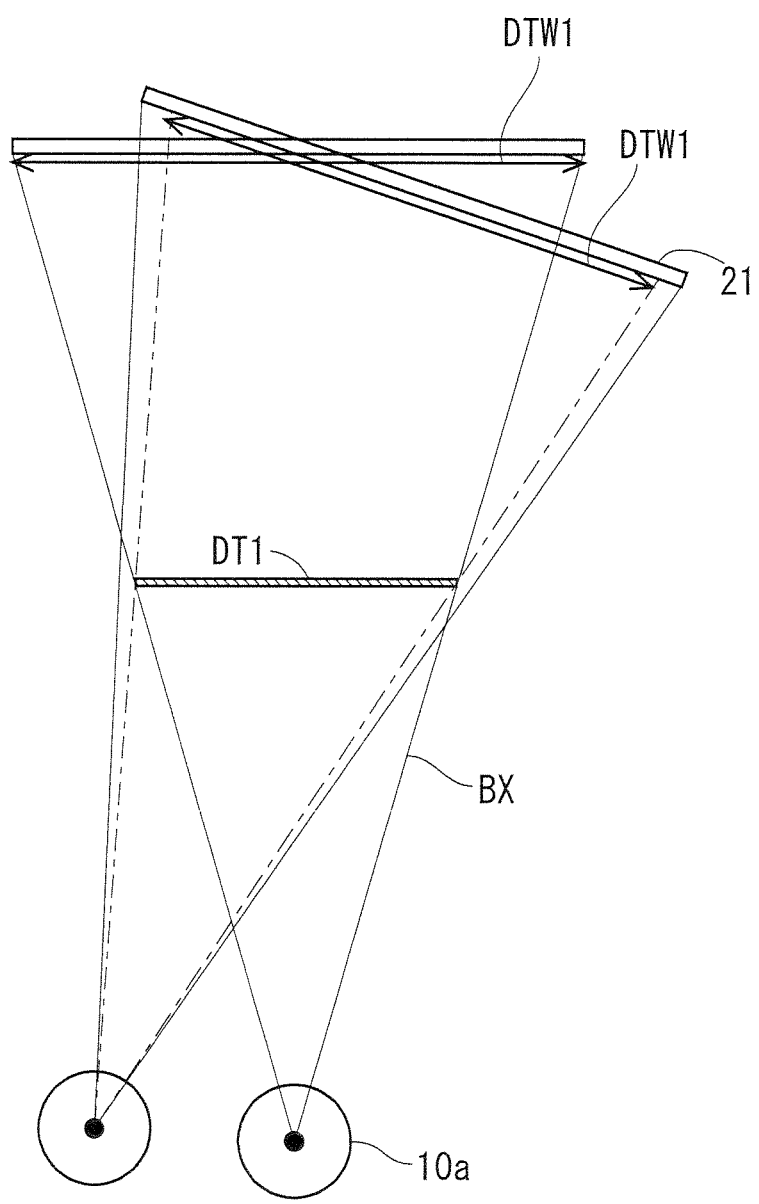
FIG. 20 is an explanatory view illustrating a relationship between an X-ray beam and a target cross-section.

FIG. 20 is an explanatory view indicating a relationship between the X-ray beam BX and a target cross-section DT1. As indicated in FIG. 20, in the case that a fan angle (a horizontal spread angle) of the X-ray beam BX is kept constant in the process of the X-ray photography such as the pseudo intraoral radiography, a width DTW1 of the projection image of the target cross-section DT1 expands and contracts by turning the turning arm 30. Even if the width DTW1 of the projection image varies, the width DTW1 is corrected by the calculation processing, which allows the tomographic image to be reconstructed without any difficulty.

The principle of the method of stacking based on the shift-and-add method is described above. The filtered back projection will be described below.

<Filtered Back Projection>

The X-ray photography apparatus 1 generates the tomographic image by applying the filtered back projection (FBP) different from the method of stacking to the frame data acquired by the pseudo intraoral radiography.

FIG. 21 is a view indicating the filtered back projection to which a filter function F1 is applied. FIG. 22 is a view indicating the filtered back projection to which a filter function F2 is applied. In the filtered back projection, similarly to the conventional process of generating the CT image, after a one-dimensional Fourier transform is performed to the frame data expressing the X-ray projection image, a convolution filter (the filter function F1 or the filter function F2) is applied before a back projection (specifically, a one-dimensional inverse Fourier transform) is performed to obtain a subject distribution. The filter function F1 has a "negative" origin, and the filter function F1 comes close to 0 when leaving the origin. The filter function F2 has a "positive" origin, and surroundings of the origin are "negative". The filter function is not limited to the filter functions F1 and F2 in FIGS. 21 and 22, but various filter functions may be used. The filter function may properly be selected according to the photographing target object.

Figure 23:
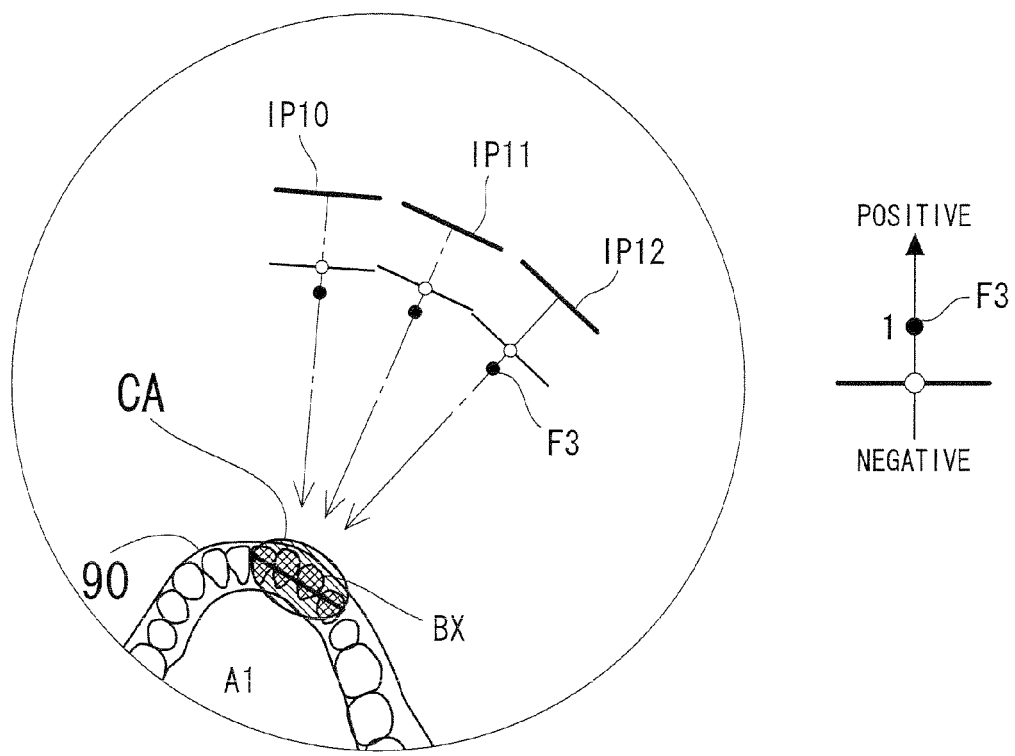
FIG. 23 is a view illustrating the filtered back projection to which a filter function equivalent to a method of stacking is applied.

FIG. 23 is a view indicating the filtered back projection to which a filter function F3 equivalent to the method of stacking is applied. The filter function F3 has the origin of "1", and the filter function F3 except the origin has a value of "0". The use of the filter function F3 results in generating the tomographic image equivalent to the tomographic image acquired by the method of stacking.

It is assumed that BP1 is the filtered back projection in which the filter function F1 is used, that BP2 is the filtered back projection in which the filter function F2 is used, and that BP3 is the filtered back projection in which the filter function F3 is used. The filter functions F1, F2, and F3 can be used such that the filtered back projections BP1, BP2, and BP3 become the pieces of image processing in which the information content related to the X-ray absorption before and behind the specific tomographic plane differ from one another.

In the filtered back projection, after the filter function is applied to the projection data in a frequency space after the one-dimensional Fourier transform, the one-dimensional inverse Fourier transform (that is, the back projection) is performed to acquire the three-dimensional data (voxel data) expressing the original photographic region CA. The tomographic image expressing the target cutting plane is generated from the three-dimensional data.

According to the filtered back projection, the tomographic image depending on an X-ray absorption coefficient of the object existing on the target cutting plane is obtained, so that a clear outline of the object can visually be recognized. In other words, the image is obtained while the information content related to the X-ray absorption of the object existing before and behind the target cutting plane are substantially eliminated. However, in the case that a material such as a metal which has the high X-ray absorption coefficient exists, occasionally the material is photographed as metallic artifact in the image.

On the other hand, in the method of stacking (the shift-and-add method), because the object located before and behind the target cutting plane is also photographed in the tomographic image as indicated in FIG. 19, the outline is slightly blurred in the image. However, in the image diagnosis, the tomographic image obtained by the method of stacking is extremely effective in that the metallic artifact generated in the filtered back projection is not generated.

Using the plural convolution filter functions different from each other, the plural tomographic images may be generated based on the filtered back projection. Therefore, the plural tomographic images in which the information content related to the object located before and behind the target cutting plane differ from each other are obtained to enable the reader to select the image more suitable for the diagnosis.

By generating the plural tomographic images having different information content related to the X-ray absorption before and behind the target cutting plane, the plural tomographic images fitting in plural diagnostic purposes can be generated from pieces of data obtained by the identical X-ray photography. Therefore, multiple image diagnosis can be made. Additionally, the proper image diagnosis can be made by selecting the better tomographic image fitting in the diagnostic purpose from the plural tomographic images.

The tomographic image similar to the conventional intraoral radiography (the dental radiography) can be generated by superposing the plural X-ray projection images by the method of stacking. In the tomographic image, because metallic artifact is not generated, the image diagnosis of the target place can properly be made. The tomographic image having an excellent contrast can be acquired by the filtered back projection. Therefore, the target place can be clearly observed to make the image diagnosis. The tomographic image generated by the method of stacking and the tomographic image generated by the filtered back projection are both generated, which allows the image diagnosis to be properly made while shortcomings of both tomographic images are compensated.

<Operation Flow of X-Ray Photography Apparatus>

Figure 24:
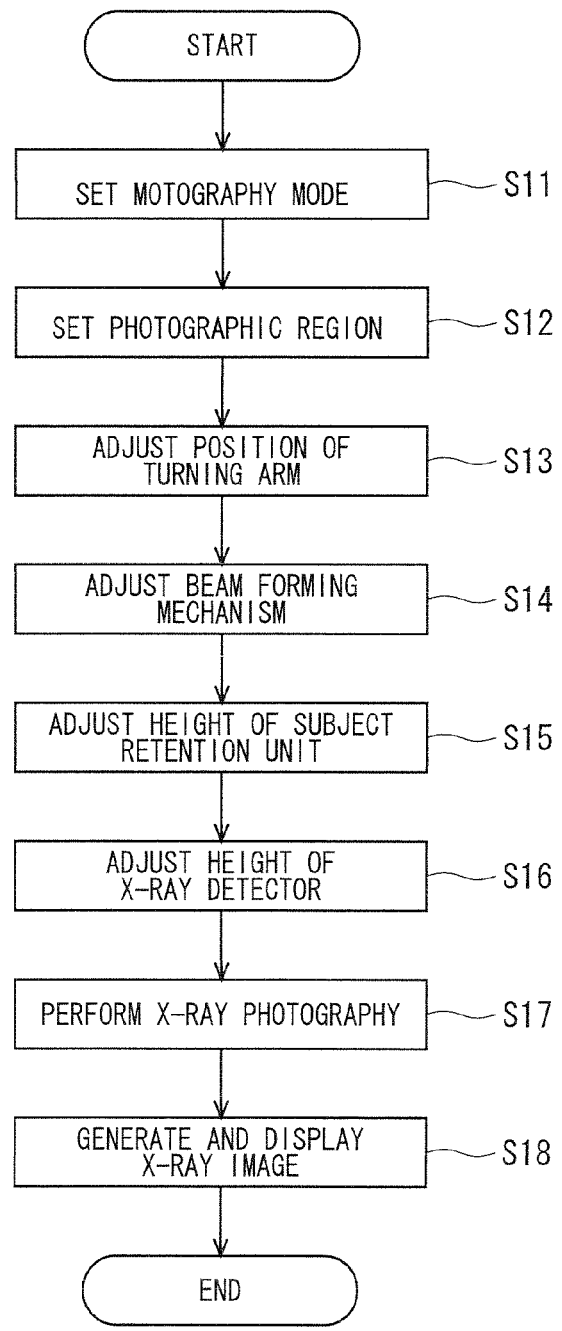
FIG. 24 is a flowchart illustrating the X-ray photography of the X-ray photography apparatus.

FIG. 24 is a flowchart indicating the X-ray photography of the X-ray photography apparatus 1. The operation of the X-ray photography apparatus 1 is mainly performed under the control of the main body controller 60 unless otherwise noted.

When the X-ray photography is started, the photography mode is set first (Step S11 in FIG. 24). Specifically, the photography mode selection screen MSW in FIG. 11 is displayed, and the mode setter 601 sets the photography mode of the main body 2 based on the manipulation input of the operator through the photography mode selection screen MSW.

Then the photographic region is designated (Step S12 in FIG. 24). More specifically, for the pseudo intraoral radiography, the upper jaw or the lower jaw and the tooth are designated (the tooth of the photographing target is designated through the photographic region setting screen 300 or a number allocated to each tooth on the region screen is designated). For the panoramic photography, all the jaws including the upper jaw and the lower jaw or one of the upper jaw and the lower jaw are designated. For the CT photography, the size and the position of the photographic region are designated through the photographic region setting screen 300.

The position of the turning arm 30 is adjusted after the designation of the photographic region (Step S13 in FIG. 24). Specifically, the height of the turning arm 30, the horizontal two-dimensional position of the turning arm 30, and the turning starting position of the turning arm 30 are adjusted so as to fit to each photography mode and the photographic region. The adjustment of the X-ray beam forming mechanism 13 (Step S14 in FIG. 24) and the height adjustment of the subject retention part 421 in the case that the subject retention part 421 can be elevated (Step S15 in FIG. 24) are performed as needed basis. The irradiation range and the irradiation direction of the X-ray beam BX and the height of the X-ray beam BX are adjusted accordingly. The height adjustment (Step S16 in FIG. 24) of the X-ray detector 21 is performed as needed basis.

When the adjustment of each component is completed, the main body 2 performs the X-ray photography (Step S17 in FIG. 24). Specifically, in the main body 2, the turning arm 30 is turned to move the X-ray generator 10a and the X-ray detector 21 on a locus corresponding to each photography mode and the photographic region, and the X-ray generator 10a emits the X-ray beam BX having a predetermined shape. The main body 2 detects the X-ray beam BX with the X-ray detector 21, and outputs the frame data to the image processing device 8.

When the frame data is collected, the X-ray photography apparatus 1 performs the image processing with the image processing device 8 to generate the X-ray image according to the photography mode, and displays the X-ray image on the display part 81 (Step S18 in FIG. 24). The flow of the basic action of the X-ray photography apparatus 1 is described above. The image generation processing and the display processing in Step S18 in the case that the pseudo intraoral radiography mode is selected in Step S11 will be described below in detail.

Figure 25:
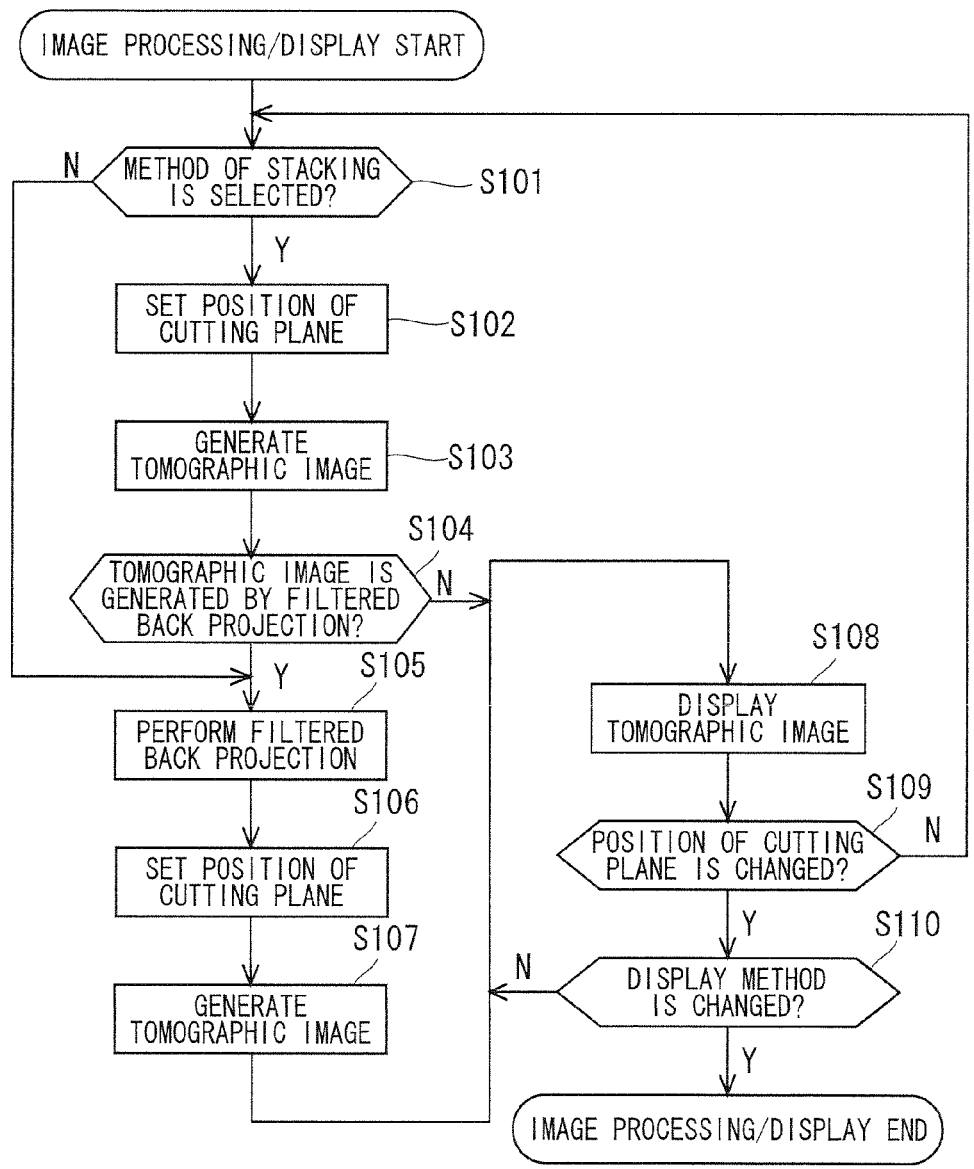
FIG. 25 is a detailed flowchart illustrating image generation processing and display processing in a pseudo intraoral radiography mode.

FIG. 25 is a detailed flowchart indicating the image generation processing and the display processing in the pseudo intraoral radiography mode. Firstly, when the frame data is collected by the pseudo intraoral radiography, whether the tomographic image is generated by the method of stacking is determined (Step S101 in FIG. 25). When not the method of stacking but the filtered back projection is selected as the image generation method in Step S101, the X-ray photography apparatus 1 goes to Step S105. Specifically, an image generation method selection screen (not illustrated) is displayed on the display part 81, and the operator selects the method for generating the tomographic image through the manipulation part 82. The manipulation part 82 thus acts as the image processing method selector (see FIG. 3).

When the performance of the method of stacking is selected in Step S101, the position of the cutting plane is set (Step S102 in FIG. 25). At this point, the position of the cutting plane is temporarily set to an arbitrary initial position. The tomographic image related to the set cutting plane is generated by performing the method of stacking (the shift-and-add method) (Step S103 in FIG. 25).

The X-ray photography apparatus 1 determines whether the tomographic image needs to be generated by the filtered back projection (Step S104 in FIG. 25). When the tomographic image needs to be generated by the filtered back projection, the filtered back projection is performed (Step S105 in FIG. 25). The contents of the filtered back projection are already described with reference to FIGS. 21 and 22. When the tomographic image needs not to be generated by the filtered back projection, the X-ray photography apparatus 1 goes to Step S108.

When the filtered back projection is performed, the position of the cutting plane is set (Step S106 in FIG. 25). In Step S106, similarly to Step S102, the position of the cutting plane is temporarily set to an arbitrary initial position. The tomographic image related to the set cutting plane is generated based on the three-dimensional data generated by the filtered back projection (Step S107 in FIG. 25).

The tomographic image obtained by the method of stacking, the tomographic image obtained by the filtered back projection, or the tomographic image obtained by the method of stacking and the filtered back projection is generated, and the X-ray photography apparatus 1 displays the generated tomographic image on the display part 81 (Step S108).

The X-ray photography apparatus 1 determines whether the position of the cutting plane is changed (Step S109). When the position of the cutting plane is changed, the X-ray photography apparatus 1 returns to Step S101 to set the position of the cutting plane by the method of stacking or the filtered back projection (Steps S102 and S106 in FIG. 25). The tomographic image related to the new position of the cutting plane is generated (Steps S103 and S107 in FIG. 25).

The position of the cutting plane is changed based on a given manipulation that is input through the manipulation part 82. At this point, for example, as indicated in FIG. 18, the images of the standard dental arch 90 and the cutting plane (for example, the planar cutting plane A1) may be displayed on the display part 81, and the cutting plane may be moved back and forth to finally determine the position. At this point, the shape of the cutting plane may be changed. Step S110 is described later.

FIG. 26 is a view indicating display examples of a tomographic image Ti1 of the method of stacking and a tomographic image Ti2 of the filtered back projection. As indicated in FIG. 26, the tomographic image Ti1 of the method of stacking is similar to the X-ray image obtained by the conventional intraoral radiography. Compared with the tomographic image Ti1, the tomographic image Ti2 of the filtered back projection has excellent contrast, clear outline, and easy-to-understand structure of the tooth or the gum. However, the artifact is easily generated in the filtered back projection. Accordingly, because the tomographic image Ti1 of the method of stacking can be used even if the artifact is generated, the image diagnosis can properly be made.

FIG. 26 illustrates an example in which the tomographic images Ti1 and Ti2 are simultaneously displayed. Alternatively, the tomographic images Ti1 and Ti2 may sequentially be displayed. In other words, the tomographic images Ti1 and Ti2 may be displayed by being switched at required time intervals.

Referring to FIG. 25, when Step S109 is completed, the X-ray photography apparatus 1 determines whether the display method is changed (Step S110). Specifically, for example, when a manipulation to select a specific tomographic image is performed while the plural tomographic images are displayed, the specific tomographic image is highlighted compared with the remaining tomographic images. For example, the specific tomographic image is selected through the manipulation part 82. In other words, the manipulation part 82 acts as the image selector that receives the input manipulation to select the specific tomographic image.

There are the following modes in each of which the specific tomographic image is highlighted: (a) a mode in which the remaining one or more tomographic images are not displayed, (b) a mode in which the specific tomographic image is displayed larger than the remaining tomographic images, (c) a mode in which the specific tomographic image is displayed on the previously-acquired panoramic image of the whole dental arch, and (d) a mode in which a frame FR1 (see FIG. 26) indicating a selection is displayed on the selected specific tomographic image.

In the mode (c), the panoramic image previously obtained by the panoramic photography with the X-ray photography apparatus 1 may be used, or the panoramic image obtained with another X-ray photography apparatus may be used. In the mode (c), in the panoramic image, a portion on which the specific tomographic image is superposed may go blank by discarding the data, and the specific tomographic image may be displayed while fitted in the blank portion. Alternatively, the tomographic image may be displayed overlapping a complete panoramic image as another layer.

The highlighting mode is not limited to the modes (a) to (d), but any display mode may be used as long as the specific tomographic image is displayed so as to attract operator's attention compared with other tomographic images.

As described above, by highlighting the selected specific tomographic image, the reader can make the image diagnosis while concentrating on the highlighted tomographic image.

In the case that the plural tomographic images are displayed, the change of the position of the cutting plane in Step S109 of FIG. 25 may be performed to the plural tomographic images or only one of the plural tomographic images. After the position of the cutting plane is changed for one of the plural tomographic images, the position of the identical cutting plane may be changed for the other tomographic image.

In the case that the position of the cutting plane is changed for the plural tomographic images, the position of the cutting plane may automatically be changed for one of the tomographic images when the position of the cutting plane is changed for the other tomographic image.

FIG. 25 illustrates an example of the process in which the tomographic image generation method is selected between the method of stacking and the filtered back projection. Alternatively, the process in FIG. 25 may be replaced by a process in which the tomographic image generation method is selected among plural filtered back projections in which different filter functions are used.

For example, it is conceivable that the tomographic image generation method is selected between the filtered back projection in which the filter function F1 is used and the filtered back projection in which the filter function F2 is used.

In this case, the image processing in Step S101 performed by the method of stacking is replaced by the filtered back projection in which the filter function F1 is used, and the filtered back projection in which the filter function F2 is used is used as the image processing in Step S105 performed by the filtered back projection.

The number of tomographic images that should be displayed is not limited to two. For example, three tomographic images including the tomographic image obtained by using the method of stacking, the tomographic image obtained by the filtered back projection BP1, and the tomographic image obtained by the filtered back projection BP2 may be generated and displayed; and three tomographic images including the tomographic image obtained by the filtered back projection BP1, the tomographic image obtained by the filtered back projection BP2, and the tomographic image obtained by the filtered back projection BP3 may be generated and displayed; or at least four tomographic images may be generated and displayed.

Figure 27:
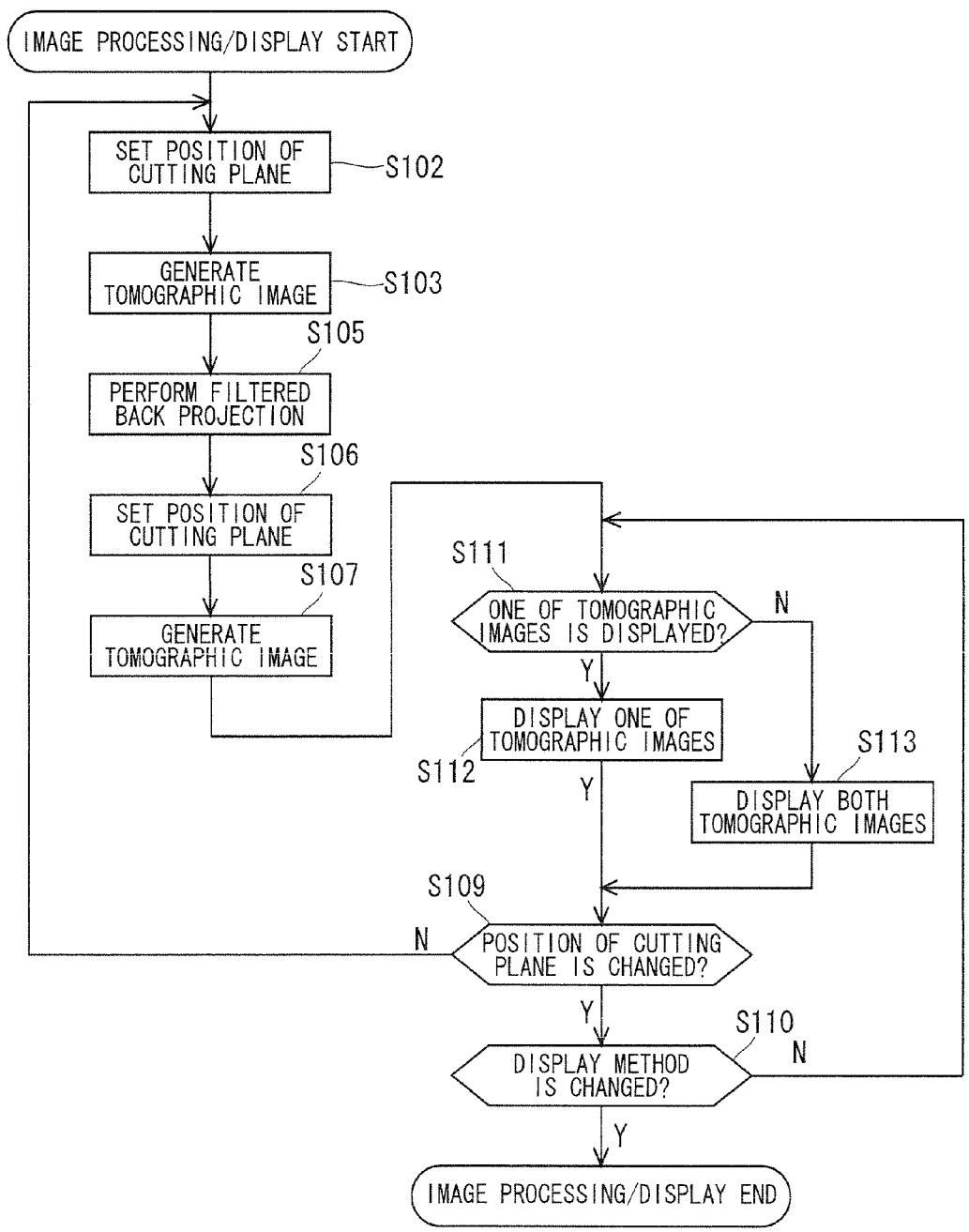
FIG. 27 is another detailed flowchart illustrating the image generation processing and the display processing in the pseudo intraoral radiography mode.

FIG. 27 is another detailed flowchart indicating the image generation processing and the display processing in the pseudo intraoral radiography mode. In the steps of the flowchart in FIG. 27, a step similar to the step of the flowchart in FIG. 25 is designated by the identical numeral. In the flowchart in FIG. 25, the tomographic image generation method is selected between the method of stacking and the filtered back projection. On the other hand, in the flowchart in FIG. 27, the selection step is eliminated, and the tomographic image is generated by applying the method of stacking and the filtered back projection.

In the flowchart in FIG. 27, whether only one of the tomographic image obtained by the method of stacking and the tomographic image obtained by the filtered back projection is displayed is determined after the tomographic images are generated (Step S111 in FIG. 27). A selection screen is displayed on the display part 81, and the selection manipulation is performed through the manipulation part 82. Specifically, one of the display of only the tomographic image obtained by the method of stacking, the display of only the tomographic image obtained by the filtered back projection, and the display of the both tomographic images is selected on the selection screen. In other words, the manipulation part 82 acts as the display image selector. The determination in Step S111 is made based on the selection manipulation. Based on the determination in Step S111, one of the tomographic images is displayed (Step S112 in FIG. 27) or both tomographic images are displayed (Step S113 in FIG. 27).

The flow of the preferred embodiment is described above.

In the configuration of the image processing performed by the method of stacking in FIG. 19, processing of removing a shade that is an obstacle may further be performed in order to improve image quality. Particularly, according to the mechanical configuration of the X-ray photography apparatus, occasionally, the X-ray beam passes through a site, such as a cervical spine, which is not clear in the X-ray image data and provides shade that is the obstacle of reading, when the X-ray photography is performed to the pseudo intraoral radiography region. Hereinafter, the site is referred to as an obstacle shade causal site.

For example, the tomographic image data of the obstacle shade causal site photographed in the frame data obtained by the pseudo intraoral radiography can be generated by applying the image processing performed by the method of stacking. Based on the tomographic image data of the obstacle shade causal site, a blurred image can be generated by simulating by the calculation the case that the image of the obstacle shade causal site is projected to the target cutting plane of the pseudo intraoral radiography, and the processing of subtracting the blurred image from the tomographic image of the target cutting plane of the pseudo intraoral radiography can be performed.

The image processing is disclosed in Japanese Patent Application Laid-Open No. H04-144548 filed by the applicant of the present application, and can properly be applied to the present invention. Although the technology disclosed in Japanese Patent Application Laid-Open No. H04-144548 relates to a panoramic image, the obstacle shade removing technique can be applied to the image processing in FIG. 19. The image processing may be performed by the filtered back projection in generating the tomographic image data of the obstacle shade causal site.

The X-ray photography apparatus 1 according to the preferred embodiment of the present invention is configured to be able to perform the pseudo intraoral radiography, the panoramic photography, the CT photography, and the cephalic photography. However, the X-ray photography apparatus according to the present invention may be configured to be able to perform at least one of the panoramic photography, the CT photography, and the cephalic photography together with the pseudo intraoral radiography.

While the invention is shown and described in detail in the above, the foregoing description is in all aspects illustrative and not restrictive. It should be, therefore, understood that numerous modifications and variations can be devised without departing from the scope of the invention.

What is claimed is:

1. An X-ray photography apparatus comprising:
   a support that supports an X-ray generator and an X-ray detector while said X-ray generator and said X-ray detector are opposed to each other so that a head of a patient can be interposed therebetween, said X-ray detector outputting an electric signal according to an intensity of an incident X-ray;
   a moving mechanism that includes a turning part and a moving part, the turning part relatively turning said X-ray generator and said X-ray detector about head by turning said support relative to said head about a predetermined turning axis, and the moving part relatively moving said support to said head in a direction perpendicular to said turning axis;

an image processor that generates a tomographic image related to a specific tomographic plane from a projection image of an X-ray based on said electric signal output from said X-ray detector;

a photographic region designation receiving part that receives an operation to designate a region including a row of teeth or part of a gum as a pseudo intraoral radiography region, said row of teeth or said gum being spread along a curve of a dental arch; and a controller that performs pseudo intraoral radiography to said pseudo intraoral radiography region in which designation is received by said photographic region designation receiving part, the X-ray generator irradiating said pseudo intraoral radiography region with the X-ray, said image processor performing different methods of image processing to X-ray image data obtained by said pseudo intraoral radiography, and generating a plurality of tomographic images in which information contents related to X-ray absorption before and behind said specific tomographic plane differ from each other.

2. The X-ray photography apparatus according to claim 1, said plurality of tomographic images including a tomographic image that is generated by method of stacking a plurality of projection images and a tomographic image that is generated by a filtered back projection.

3. The X-ray photography apparatus according to claim 2, said filtered back projection using a convolution filter.

4. The X-ray photography apparatus according to claim 2, said plurality of tomographic images including a plurality of tomographic images which are generated by said filtered back projection in which convolution filters different from each other are used.

5. The X-ray photography apparatus according to claim 1, said X-ray generator emitting an X-ray beam of an irradiation range that includes a whole region of said pseudo intraoral radiography region.

6. The X-ray photography apparatus according to claim 1, further comprising an irradiation direction changing part that relatively changes an irradiation direction in which said head is irradiated with an X-ray beam emitted from said X-ray generator with respect to an axial direction of a body axis of the patient, and said irradiation direction changing part changing said irradiation direction according to said pseudo intraoral radiography region.

7. The X-ray photography apparatus according to claim 6, said controller performing CT photography by turning said support about said turning axis relative to said head by at least 180 degrees, and said irradiation direction changing part changing said irradiation direction between said CT photography and said pseudo intraoral radiography.

8. The X-ray photography apparatus according to claim 1, further comprising a display part that simultaneously or sequentially displays said plurality of tomographic images generated by said image processor.

9. The X-ray photography apparatus according to claim 8, further comprising an image selector that receives an input operation to select a specific tomographic image from said plurality of tomographic images, and said display part highlighting said specific tomographic image selected by said image selector compared with one or more residual tomographic images that are not selected.

10. The X-ray photography apparatus according to claim 9, said display part performing, when highlighting said specific tomographic image, at least one of the followings:
(a) said one or more residual tomographic images are not displayed,
(b) said specific tomographic image is displayed while enlarged compared with said one or more residual tomographic images,
(c) said specific tomographic image is displayed on a previously-acquired panoramic image of a whole dental arch, and
(d) a frame indicating a selection is displayed on said selected specific tomographic image.

11. The X-ray photography apparatus according to claim 1, said controller performing CT photography by turning said support about said turning axis relative to said head by at least 180 degrees.

12. The X-ray photography apparatus according to claim 11, said X-ray detector changing spatial resolution in detecting the X-ray between said pseudo intraoral radiography and said CT photography.

13. The X-ray photography apparatus according to claim 11, said photographic region designation receiving part displaying a region designating image in order to designate a region where said CT photography is performed, and receiving an input operation to the region designating image.

14. The X-ray photography apparatus according to claim 1, said controller moving said support relative to said head, irradiating said dental arch with an X-ray slit beam from said X-ray generator, and performing panoramic photography.

15. The X-ray photography apparatus according to claim 14, said X-ray detector changing spatial resolution in detecting the X-ray between said pseudo intraoral radiography and said panoramic photography.

16. The X-ray photography apparatus according to claim 14, said controller changing a magnification rate of an X-ray image to be acquired between said pseudo-intraoral radiography and said panoramic photography by changing a distance from said X-ray detector to said head.

17. The X-ray photography apparatus according to claim 14, said panoramic photography being partial panoramic photography in which part of a region of said dental arch is set to a photography target.

18. The X-ray photography apparatus according to claim 1, said photographic region designation receiving part displaying a region designating image in order to designate said pseudo intraoral radiography region, and receives an input operation to the region designating image.

19. The X-ray photography apparatus according to claim 18, said region designating image being a panoramic image of said dental arch.

* * * * *